(12) United States Patent
Quadri et al.

(10) Patent No.: US 10,888,414 B2
(45) Date of Patent: Jan. 12, 2021

(54) AORTIC DISSECTION IMPLANT

(71) Applicant: inQB8 Medical Technologies, LLC, Winchester, MA (US)

(72) Inventors: Arshad Quadri, West Hartford, CT (US); J. Brent Ratz, Winchester, MA (US); Christopher William Stivers, Somerville, MA (US)

(73) Assignee: inQB8 Medical Technologies, LLC, Winchester, MA (US)

( * ) Notice: Subject to any disclaimer, the term of this patent is extended or adjusted under 35 U.S.C. 154(b) by 0 days.

(21) Appl. No.: 16/824,029

(22) Filed: Mar. 19, 2020

(65) Prior Publication Data
US 2020/0297475 A1 Sep. 24, 2020

Related U.S. Application Data

(60) Provisional application No. 62/821,052, filed on Mar. 20, 2019.

(51) Int. Cl.
*A61F 2/07* (2013.01)
(52) U.S. Cl.
CPC ........ *A61F 2/07* (2013.01); *A61F 2210/0076* (2013.01); *A61F 2230/0091* (2013.01);
(Continued)
(58) Field of Classification Search
CPC .............. A61F 2/07; A61F 2250/0024; A61F 2002/077; A61F 2002/068; A61F 2/82
See application file for complete search history.

(56) References Cited

U.S. PATENT DOCUMENTS

| 4,313,231 A | 2/1982 | Koyamada |
| 4,577,631 A | 3/1986 | Kreamer |
| 4,820,298 A | 4/1989 | Leveen et al. |
| 4,994,071 A | 2/1991 | MacGregor |
| 5,102,417 A | 4/1992 | Palmaz |

(Continued)

FOREIGN PATENT DOCUMENTS

| AU | 2007201644 A1 | 5/2007 |
| EP | 0335341 A1 | 10/1989 |

(Continued)

OTHER PUBLICATIONS

International Search Report and Written Opinion in PCT/US2020/023651, dated Jun. 17, 2020, in 17 pages.

*Primary Examiner* — Dinah Baria
(74) *Attorney, Agent, or Firm* — Knobbe, Martens, Olson & Bear LLP

(57) ABSTRACT

A system for treating aortic dissection including an aortic dissection implant comprising an expandable anchoring structure and an elongate tubular structure. The expandable anchoring structure can be configured to apply radial force to the sinuses of the aortic root and/or the sinotubular junction when expanded. The elongate tubular structure can comprise an expandable support frame and one or more layers. The expandable support frame can be configured to extend from the descending aorta to the ascending aorta and curve along with a curvature of the aortic arch when expanded within the aorta. The one or more layers can comprise a first porous layer comprising an atraumatic outer surface positioned over the expandable support frame and a second non-porous layer positioned over a portion of the first porous layer. The second non-porous layer may be configured to be positioned on opposite sides of the aortic dissection and to be inflatable via blood flow to seal against the dissection.

28 Claims, 21 Drawing Sheets

(52) U.S. Cl.
CPC ............... *A61F 2250/0024* (2013.01); *A61F 2250/0059* (2013.01)

(56) References Cited

U.S. PATENT DOCUMENTS

| | | |
|---|---|---|
| 5,133,732 A | 7/1992 | Wiktor |
| 5,195,984 A | 3/1993 | Schatz |
| 5,207,695 A | 4/1993 | Trout, III |
| 5,211,658 A | 5/1993 | Clouse |
| 5,316,023 A | 5/1994 | Palmaz et al. |
| 5,360,443 A | 11/1994 | Barone et al. |
| 5,387,235 A | 2/1995 | Chuter |
| 5,464,449 A | 11/1995 | Ryan et al. |
| 5,489,295 A | 2/1996 | Piplani et al. |
| 5,507,769 A | 4/1996 | Marin et al. |
| 5,507,770 A | 4/1996 | Turk |
| 5,562,724 A | 10/1996 | Vorwerk et al. |
| 5,578,071 A | 11/1996 | Parodi |
| 5,591,195 A | 1/1997 | Taheri et al. |
| 5,591,230 A | 1/1997 | Taheri et al. |
| 5,665,117 A | 9/1997 | Rhodes |
| 5,676,697 A | 10/1997 | McDonald |
| 5,683,449 A | 11/1997 | Marcade |
| 5,683,450 A | 11/1997 | Goicoechea et al. |
| 5,733,325 A | 3/1998 | Robinson et al. |
| 5,741,325 A | 4/1998 | Chaikof et al. |
| 5,755,773 A | 5/1998 | Evans et al. |
| 5,776,185 A | 7/1998 | Verona et al. |
| 5,782,904 A | 7/1998 | White et al. |
| 5,782,905 A | 7/1998 | Richter |
| 5,824,040 A | 10/1998 | Cox et al. |
| 5,824,041 A | 10/1998 | Lenker et al. |
| 5,827,321 A | 10/1998 | Roubin et al. |
| 5,843,164 A | 12/1998 | Frantzen et al. |
| 5,861,025 A | 1/1999 | Boudghene et al. |
| 5,871,537 A | 2/1999 | Holman et al. |
| 5,906,641 A | 5/1999 | Thompson et al. |
| 5,925,076 A | 7/1999 | Inoue |
| 5,968,090 A | 10/1999 | Ratcliff et al. |
| 6,015,431 A | 1/2000 | Thornton et al. |
| 6,016,810 A | 1/2000 | Ravenscroft |
| 6,051,020 A | 4/2000 | Goicoechea et al. |
| 6,051,021 A | 4/2000 | Frid |
| 6,077,296 A | 6/2000 | Shokoohi et al. |
| 6,096,072 A | 8/2000 | Kanesaka et al. |
| 6,098,630 A | 8/2000 | Papazoglou |
| 6,099,548 A | 8/2000 | Taheri |
| 6,099,558 A | 8/2000 | White et al. |
| 6,102,940 A | 8/2000 | Robichon et al. |
| 6,106,549 A | 8/2000 | Taheri |
| 6,113,621 A | 9/2000 | Wiktor |
| 6,123,723 A | 9/2000 | Kónya et al. |
| 6,129,755 A | 10/2000 | Mathis et al. |
| 6,129,756 A | 10/2000 | Kugler et al. |
| 6,143,022 A | 11/2000 | Shull et al. |
| 6,149,682 A | 11/2000 | Frid |
| 6,162,246 A | 12/2000 | Barone |
| 6,168,610 B1 | 1/2001 | Marin et al. |
| 6,190,406 B1 | 2/2001 | Duerig et al. |
| 6,203,568 B1 | 3/2001 | Lombardi et al. |
| 6,214,036 B1 | 4/2001 | Letendre et al. |
| 6,221,096 B1 | 4/2001 | Aiba et al. |
| 6,224,609 B1 | 5/2001 | Ressemann et al. |
| 6,261,305 B1 | 7/2001 | Marotta et al. |
| 6,273,909 B1 | 8/2001 | Kugler et al. |
| 6,280,466 B1 | 8/2001 | Kugler et al. |
| 6,290,731 B1 | 9/2001 | Solovay et al. |
| 6,306,164 B1 | 10/2001 | Kujawski |
| 6,312,462 B1 | 11/2001 | McDermott et al. |
| 6,325,819 B1 | 12/2001 | Pavcnik et al. |
| 6,334,869 B1 | 1/2002 | Leonhardt et al. |
| 6,348,066 B1 | 2/2002 | Pinchuk et al. |
| 6,352,561 B1 | 3/2002 | Leopold et al. |
| 6,375,676 B1 | 4/2002 | Cox |
| 6,395,018 B1 | 5/2002 | Castaneda |
| 6,402,779 B1 | 6/2002 | Colone et al. |
| 6,409,750 B1 | 6/2002 | Hyodoh et al. |
| 6,478,813 B1 | 11/2002 | Keith et al. |
| 6,491,719 B1 | 12/2002 | Fogarty et al. |
| 6,500,202 B1 | 12/2002 | Shaolian et al. |
| 6,508,835 B1 | 1/2003 | Shaolian et al. |
| 6,554,858 B2 | 4/2003 | Dereume et al. |
| 6,569,190 B2 | 5/2003 | Whalen, II et al. |
| 6,585,758 B1 | 7/2003 | Chouinard et al. |
| 6,592,614 B2 | 7/2003 | Lenker et al. |
| 6,613,078 B1 | 9/2003 | Barone |
| 6,626,938 B1 | 9/2003 | Butaric et al. |
| 6,656,214 B1 | 12/2003 | Fogarty et al. |
| 6,656,219 B1 | 12/2003 | Wiktor |
| 6,695,876 B1 | 2/2004 | Marotta et al. |
| 6,699,277 B1 | 3/2004 | Freidberg et al. |
| 6,723,116 B2 | 4/2004 | Taheri |
| 6,770,090 B2 | 8/2004 | Gantt et al. |
| 6,773,454 B2 | 8/2004 | Wholey et al. |
| 6,773,457 B2 | 8/2004 | Ivancev et al. |
| 6,793,671 B2 | 9/2004 | Wall |
| 6,814,752 B1 | 11/2004 | Chuter |
| 6,827,735 B2 | 12/2004 | Greenberg |
| 6,881,221 B2 | 4/2005 | Golds |
| 6,887,268 B2 | 5/2005 | Butaric et al. |
| 6,916,337 B2 | 7/2005 | Roth |
| 6,918,925 B2 | 7/2005 | Tehrani |
| 6,923,828 B1 | 8/2005 | Wiktor |
| 6,945,991 B1 | 9/2005 | Brodeur et al. |
| 6,951,572 B1 | 10/2005 | Douglas |
| 6,960,217 B2 | 11/2005 | Bolduc |
| 6,964,679 B1 | 11/2005 | Marcade et al. |
| 6,969,401 B1 | 11/2005 | Marotta et al. |
| 6,974,471 B2 | 12/2005 | Van Schie et al. |
| 7,000,649 B2 | 2/2006 | Takahashi et al. |
| 7,011,674 B2 | 3/2006 | Brenneman |
| 7,014,653 B2 | 3/2006 | Ouriel et al. |
| 7,025,778 B2 | 4/2006 | Hayashi et al. |
| 7,029,496 B2 | 4/2006 | Rakos et al. |
| 7,033,389 B2 | 4/2006 | Sherry |
| 7,074,235 B1 | 7/2006 | Roy |
| 7,105,017 B2 | 9/2006 | Kerr |
| 7,105,020 B2 | 9/2006 | Greenberg et al. |
| 7,147,660 B2 | 12/2006 | Chobotov et al. |
| 7,160,318 B2 | 1/2007 | Greenberg et al. |
| 7,175,652 B2 | 2/2007 | Cook et al. |
| 7,175,657 B2 | 2/2007 | Khan et al. |
| 7,192,441 B2 | 3/2007 | Sherry |
| 7,201,769 B2 | 4/2007 | Jones et al. |
| 7,229,472 B2 | 6/2007 | DePalma et al. |
| 7,261,733 B1 | 8/2007 | Brown et al. |
| 7,267,685 B2 | 9/2007 | Butaric et al. |
| 7,273,491 B2 | 9/2007 | Fischell et al. |
| 7,294,147 B2 | 11/2007 | Hartley |
| 7,314,483 B2 | 1/2008 | Landau et al. |
| 7,318,835 B2 | 1/2008 | Berra |
| 7,320,703 B2 | 1/2008 | DiMatteo et al. |
| 7,326,237 B2 | 2/2008 | DePalma et al. |
| 7,344,562 B2 | 3/2008 | Feller et al. |
| 7,347,869 B2 | 3/2008 | Hojeibane et al. |
| 7,393,357 B2 | 7/2008 | Stelter et al. |
| 7,407,509 B2 | 8/2008 | Greenberg et al. |
| 7,410,665 B2 | 8/2008 | Ragheb et al. |
| 7,435,253 B1 | 10/2008 | Hartley et al. |
| 7,438,721 B2 | 10/2008 | Doig et al. |
| 7,488,344 B2 | 2/2009 | Hartley et al. |
| 7,520,895 B2 | 4/2009 | Douglas et al. |
| 7,530,988 B2 | 5/2009 | Evans et al. |
| 7,537,606 B2 | 5/2009 | Hartley et al. |
| 7,575,590 B2 | 8/2009 | Watson |
| 7,588,596 B2 | 9/2009 | Spiridigliozzi et al. |
| 7,588,597 B2 | 9/2009 | Frid |
| 7,632,304 B2 | 12/2009 | Park |
| 7,655,036 B2 | 2/2010 | Goodson |
| 7,655,037 B2 | 2/2010 | Fleming, III et al. |
| 7,666,220 B2 | 2/2010 | Evans et al. |
| 7,670,369 B2 | 3/2010 | Schaeffer |
| 7,678,141 B2 | 3/2010 | Greenan et al. |
| 7,682,380 B2 | 3/2010 | Thornton et al. |

(56) References Cited

U.S. PATENT DOCUMENTS

| | | |
|---|---|---|
| 7,682,383 B2 | 3/2010 | Robin |
| 7,686,842 B2 | 3/2010 | Pavcnik et al. |
| 7,699,883 B2 | 4/2010 | Douglas |
| 7,699,885 B2 | 4/2010 | Leonhardt et al. |
| 7,708,773 B2 | 5/2010 | Pinchuk et al. |
| 7,758,634 B2 | 7/2010 | Brucker et al. |
| 7,763,062 B2 | 7/2010 | Spiridigliozzi et al. |
| 7,780,718 B2 | 8/2010 | Smith |
| 7,785,365 B2 | 8/2010 | Holman et al. |
| 7,789,903 B2 | 9/2010 | Spiridigliozzi et al. |
| 7,806,917 B2 | 10/2010 | Xiao |
| 7,828,839 B2 | 11/2010 | Cook et al. |
| 7,833,259 B2 | 11/2010 | Boatman |
| 7,892,277 B2 | 2/2011 | Douglas et al. |
| 7,912,554 B2 | 3/2011 | Capuano et al. |
| 7,918,800 B1 | 4/2011 | Brown et al. |
| 7,955,372 B2 | 6/2011 | Butterwick et al. |
| 7,959,662 B2 | 6/2011 | Erbel et al. |
| 7,993,383 B2 | 8/2011 | Hartley et al. |
| 7,993,386 B2 | 8/2011 | Elliott |
| 8,002,816 B2 | 8/2011 | Greenberg |
| 8,021,408 B2 | 9/2011 | Kang et al. |
| 8,021,413 B2 | 9/2011 | Dierking et al. |
| 8,048,140 B2 | 11/2011 | Purdy |
| 8,048,147 B2 | 11/2011 | Adams |
| 8,052,741 B2 | 11/2011 | Bruszewski et al. |
| 8,062,345 B2 | 11/2011 | Ouellette et al. |
| 8,062,346 B2 | 11/2011 | Quigley et al. |
| 8,066,755 B2 | 11/2011 | Zacharias et al. |
| 8,088,156 B2 | 1/2012 | Borges et al. |
| 8,118,862 B2 | 2/2012 | Saeed |
| 8,123,796 B2 | 2/2012 | Kasprzak |
| 8,163,006 B2 | 4/2012 | Feller et al. |
| 8,167,925 B2 | 5/2012 | Shaolian et al. |
| 8,167,930 B2 | 5/2012 | Allen et al. |
| 8,187,317 B2 | 5/2012 | Leprince et al. |
| 8,202,310 B2 | 6/2012 | Majercak et al. |
| 8,211,158 B2 | 7/2012 | Wolf |
| 8,226,708 B1 | 7/2012 | Murch |
| 8,236,040 B2 | 8/2012 | Mayberry et al. |
| 8,252,036 B2 | 8/2012 | Cartledge et al. |
| 8,252,039 B2 | 8/2012 | Golesworthy et al. |
| 8,257,423 B2 | 9/2012 | Kerr |
| 8,257,430 B2 | 9/2012 | Mead |
| 8,262,692 B2 | 9/2012 | Rudakov |
| 8,287,586 B2 | 10/2012 | Schaeffer et al. |
| 8,292,949 B2 | 10/2012 | Berra et al. |
| 8,293,261 B2 | 10/2012 | Nagura |
| 8,298,281 B2 | 10/2012 | Majercak et al. |
| 8,333,800 B2 | 12/2012 | Bruszewski et al. |
| 8,337,546 B2 | 12/2012 | Bruszewski |
| 8,353,943 B2 | 1/2013 | Kuppurathanam et al. |
| 8,377,110 B2 | 2/2013 | Douglas et al. |
| 8,377,113 B2 | 2/2013 | Hartley et al. |
| 8,388,679 B2 | 3/2013 | Du |
| 8,398,703 B2 | 3/2013 | Kassab et al. |
| 8,474,120 B2 | 7/2013 | Hagaman et al. |
| 8,480,725 B2 | 7/2013 | Rasmussen et al. |
| 8,486,131 B2 | 7/2013 | Shalev |
| 8,491,649 B2 | 7/2013 | Mach |
| 8,500,792 B2 | 8/2013 | Berra |
| 8,506,622 B2 | 8/2013 | Bruszewski et al. |
| 8,518,096 B2 | 8/2013 | Nelson |
| 8,523,931 B2 | 9/2013 | Mayberry et al. |
| 8,540,764 B2 | 9/2013 | Bruszewski et al. |
| 8,545,549 B2 | 10/2013 | Hartley et al. |
| 8,551,157 B2 | 10/2013 | Hamer et al. |
| 8,551,158 B2 | 10/2013 | Roeder et al. |
| 8,562,667 B2 | 10/2013 | Cox |
| 8,574,284 B2 | 11/2013 | Roeder et al. |
| 8,585,753 B2 | 11/2013 | Scanlon et al. |
| 8,603,153 B2 | 12/2013 | Haverkost |
| 8,632,581 B2 | 1/2014 | Chuter |
| 8,652,195 B2 | 2/2014 | Tani |
| 8,663,307 B2 | 3/2014 | Arbefeuille |
| 8,663,310 B2 | 3/2014 | Greenberg et al. |
| 8,663,315 B2 | 3/2014 | Hong et al. |
| 8,668,729 B2 | 3/2014 | Kaufmann et al. |
| 8,679,171 B2 | 3/2014 | Deem et al. |
| 8,702,785 B2 | 4/2014 | Khan et al. |
| 8,715,340 B2 | 5/2014 | Rudakov et al. |
| 8,728,144 B2 | 5/2014 | Fearnot |
| 8,728,145 B2 | 5/2014 | Chuter et al. |
| 8,728,148 B2 | 5/2014 | Roeder et al. |
| 8,734,501 B2 | 5/2014 | Hartley et al. |
| 8,740,963 B2 | 6/2014 | Arbefeuille et al. |
| 8,740,971 B2 | 6/2014 | Iannelli |
| 8,747,453 B2 | 6/2014 | Amplatz et al. |
| 8,747,455 B2 | 6/2014 | Greenberg |
| 8,753,386 B2 | 6/2014 | Shaw |
| 8,778,008 B2 | 7/2014 | Amplatz et al. |
| 8,845,676 B2 | 9/2014 | Monstadt et al. |
| 8,845,714 B2 | 9/2014 | DiMatteo et al. |
| 8,858,613 B2 | 10/2014 | Cragg et al. |
| 8,864,813 B2 | 10/2014 | Barr |
| 8,870,938 B2 | 10/2014 | Shalev et al. |
| 8,876,886 B2 | 11/2014 | Kaufmann et al. |
| 8,900,287 B2 | 12/2014 | Amplatz et al. |
| 8,906,081 B2 | 12/2014 | Cully et al. |
| 8,911,468 B2 | 12/2014 | Ogle et al. |
| 8,911,491 B2 | 12/2014 | Hanson et al. |
| 8,915,955 B2 | 12/2014 | West et al. |
| 8,915,956 B2 | 12/2014 | Schaeffer et al. |
| 8,926,682 B2 | 1/2015 | Herbowy et al. |
| 8,926,688 B2 | 1/2015 | Burkart et al. |
| 8,945,199 B2 | 2/2015 | Ganpath et al. |
| 8,945,202 B2 | 2/2015 | Mayberry et al. |
| 8,945,205 B2 | 2/2015 | Greenberg |
| 8,945,207 B2 | 2/2015 | Mattsson et al. |
| 8,951,298 B2 | 2/2015 | Shalev |
| 8,961,587 B2 | 2/2015 | Zhu et al. |
| 8,968,384 B2 | 3/2015 | Pears0n et al. |
| 8,974,518 B2 | 3/2015 | Bruszewski et al. |
| 8,992,592 B2 | 3/2015 | Molaei et al. |
| 9,005,268 B2 | 4/2015 | Hartley et al. |
| 9,005,270 B2 | 4/2015 | Perkins et al. |
| 9,005,271 B2 | 4/2015 | Ivancev et al. |
| 9,011,517 B2 | 4/2015 | Hartley et al. |
| 9,028,541 B2 | 5/2015 | Abunassar |
| 9,034,027 B2 | 5/2015 | Ivancev |
| 9,044,311 B2 | 6/2015 | Rasmussen et al. |
| 9,055,999 B2 | 6/2015 | Thomas et al. |
| 9,056,000 B2 | 6/2015 | Luo et al. |
| 9,066,824 B2 | 6/2015 | Madjarov |
| 9,095,421 B2 | 8/2015 | Peterson |
| 9,095,456 B2 | 8/2015 | Ivancev et al. |
| 9,101,506 B2 | 8/2015 | Arbefeuille et al. |
| 9,113,999 B2 | 8/2015 | Taylor et al. |
| 9,125,764 B2 | 9/2015 | Shaw |
| 9,138,228 B2 | 9/2015 | Vassiliades et al. |
| 9,149,373 B2 | 10/2015 | Davis et al. |
| 9,149,382 B2 | 10/2015 | Greenberg et al. |
| 9,155,641 B2 | 10/2015 | Schaeffer et al. |
| 9,168,162 B2 | 10/2015 | Smouse |
| 9,175,427 B2 | 11/2015 | Haselby et al. |
| 9,179,998 B2 | 11/2015 | Kölbel et al. |
| 9,186,267 B2 | 11/2015 | Losordo et al. |
| 9,211,183 B2 | 12/2015 | Ivancev et al. |
| 9,226,813 B2 | 1/2016 | Brocker et al. |
| 9,265,599 B2 | 2/2016 | Greenberg et al. |
| 9,308,079 B2 | 4/2016 | Koskas et al. |
| 9,314,327 B2 | 4/2016 | Orr |
| 9,314,353 B2 | 4/2016 | Heraty et al. |
| 9,345,594 B2 | 5/2016 | Woerne |
| 9,351,822 B2 | 5/2016 | Roeder |
| 9,393,100 B2 | 7/2016 | Schreck |
| 9,393,136 B2 | 7/2016 | Perkins et al. |
| 9,402,712 B2 | 8/2016 | Cam et al. |
| 9,402,754 B2 | 8/2016 | Chan et al. |
| 9,408,607 B2 | 8/2016 | Cartledge et al. |
| 9,408,731 B2 | 8/2016 | Hartley et al. |
| 9,427,306 B2 | 8/2016 | Shahriari |
| 9,427,339 B2 | 8/2016 | Shalev |
| 9,439,758 B2 | 9/2016 | Keeble et al. |

(56) References Cited

U.S. PATENT DOCUMENTS

| | | |
|---|---|---|
| 9,463,102 B2 | 10/2016 | Kelly |
| 9,463,105 B2 | 10/2016 | Farhat et al. |
| 9,486,341 B2 | 11/2016 | Shalev |
| 9,498,322 B2 | 11/2016 | Thomas |
| 9,498,361 B2 | 11/2016 | Roeder et al. |
| 9,526,642 B2 | 12/2016 | Arnault De La Menardiere et al. |
| 9,526,813 B2 | 12/2016 | Cohn et al. |
| 9,545,323 B2 | 1/2017 | Cully |
| 9,561,121 B2 | 2/2017 | Sudin et al. |
| 9,572,652 B2 | 2/2017 | Cragg et al. |
| 9,579,103 B2 | 2/2017 | Schreck |
| 9,585,668 B2 | 3/2017 | Rudakov et al. |
| 9,585,743 B2 | 3/2017 | Cartledge et al. |
| 9,597,204 B2 | 3/2017 | Benary et al. |
| 9,603,697 B2 | 3/2017 | Centola |
| 9,655,710 B2 | 5/2017 | Eller et al. |
| 9,662,196 B2 | 5/2017 | Roeder et al. |
| 9,668,892 B2 | 6/2017 | Shalev et al. |
| 9,687,366 B2 | 6/2017 | Golden |
| 9,717,611 B2 | 8/2017 | Jensen et al. |
| 9,724,187 B2 | 8/2017 | Ivancev et al. |
| 9,737,394 B2 | 8/2017 | Coghlan et al. |
| 9,757,260 B2 | 9/2017 | Greenan |
| 9,757,262 B2 | 9/2017 | Schreck |
| 9,757,263 B2 | 9/2017 | Roeder et al. |
| 9,763,813 B2 | 9/2017 | Park |
| 9,763,816 B2 | 9/2017 | Roeder |
| 9,770,320 B2 | 9/2017 | Eells et al. |
| 9,788,933 B2 | 10/2017 | Sun et al. |
| 9,788,934 B2 | 10/2017 | Chobotov et al. |
| 9,820,875 B2 | 11/2017 | Laduca |
| 9,833,341 B2 | 12/2017 | Bogenschuetz et al. |
| 9,839,542 B2 | 12/2017 | Bruszewski et al. |
| 9,848,869 B2 | 12/2017 | Bolduc et al. |
| 9,848,976 B2 | 12/2017 | Angel et al. |
| 9,849,006 B2 | 12/2017 | Kozyak et al. |
| 9,855,128 B2 | 1/2018 | Kölbel et al. |
| 9,861,466 B2 | 1/2018 | Havel et al. |
| 9,877,857 B2 | 1/2018 | Arbefeuille et al. |
| 9,907,642 B2 | 3/2018 | Schreck et al. |
| 9,907,681 B2 | 3/2018 | Tobis et al. |
| 9,907,683 B2 | 3/2018 | Zukowski et al. |
| 9,907,684 B2 | 3/2018 | Connor et al. |
| 9,918,861 B2 | 3/2018 | Huser et al. |
| 9,925,031 B2 | 3/2018 | Macatangay |
| 9,925,032 B2 | 3/2018 | Jensen et al. |
| 9,943,427 B2 | 4/2018 | Losordo et al. |
| 9,949,692 B2 | 4/2018 | Hunter |
| 9,949,818 B2 | 4/2018 | Kelly |
| 9,955,971 B2 | 5/2018 | Xu et al. |
| 9,968,353 B2 | 5/2018 | Bolduc et al. |
| 9,974,671 B2 | 5/2018 | Bolduc et al. |
| 9,993,328 B2 | 6/2018 | Young et al. |
| 9,993,329 B2 | 6/2018 | McDonald et al. |
| 9,993,330 B2 | 6/2018 | Roeder |
| 9,993,360 B2 | 6/2018 | Shalev et al. |
| 10,010,402 B2 | 7/2018 | Wang et al. |
| 10,010,403 B2 | 7/2018 | Marrocco et al. |
| 10,022,249 B2 | 7/2018 | Evans et al. |
| 10,028,848 B2 | 7/2018 | Shahriari |
| 10,028,849 B2 | 7/2018 | Bui et al. |
| 10,029,424 B2 | 7/2018 | Verschueren et al. |
| 10,034,785 B1 | 7/2018 | Schonholz et al. |
| 10,034,788 B2 | 7/2018 | Kasprzak, II et al. |
| 10,039,655 B2 | 8/2018 | Pung et al. |
| 10,070,950 B2 | 9/2018 | Piccagli et al. |
| 10,098,770 B2 | 10/2018 | Bolduc et al. |
| 10,105,209 B2 | 10/2018 | Kerr |
| 10,105,248 B2 | 10/2018 | Berra et al. |
| 10,137,013 B2 | 11/2018 | Giasolli et al. |
| 10,143,576 B2 | 12/2018 | Greenberg et al. |
| 10,154,894 B2 | 12/2018 | Minion |
| 10,159,557 B2 | 12/2018 | Chobotov et al. |
| 10,188,501 B2 | 1/2019 | Wang et al. |
| 10,201,413 B2 | 2/2019 | Shalev et al. |
| 10,206,798 B2 | 2/2019 | Kusleika |
| 10,213,291 B2 | 2/2019 | Berra et al. |
| 10,219,890 B2 | 3/2019 | Madjarov et al. |
| 10,226,366 B2 | 3/2019 | Wainwright et al. |
| 10,231,822 B2 | 3/2019 | Hartley |
| 10,231,857 B2 | 3/2019 | Tal |
| 10,245,166 B2 | 4/2019 | Schreck et al. |
| 10,265,200 B2 | 4/2019 | Charlebois et al. |
| 10,265,202 B2 | 4/2019 | Greenberg et al. |
| 10,271,941 B2 | 4/2019 | Wintsch et al. |
| 10,278,840 B2 | 5/2019 | Tippett et al. |
| 10,292,808 B2 | 5/2019 | Mangiardi |
| 10,292,809 B2 | 5/2019 | Kuppurathanam et al. |
| 10,299,946 B2 | 5/2019 | Roselli |
| 10,307,244 B2 | 6/2019 | Ganesan et al. |
| 10,321,985 B2 | 6/2019 | Barthold et al. |
| 10,327,782 B2 | 6/2019 | Horton |
| 10,327,924 B2 | 6/2019 | Kelly |
| 10,335,297 B2 | 7/2019 | Vong et al. |
| 10,349,946 B2 | 7/2019 | Herbowy et al. |
| 10,357,353 B2 | 7/2019 | Kelly |
| 10,357,386 B2 | 7/2019 | Schaeffer et al. |
| 10,368,977 B2 | 8/2019 | Eller et al. |
| 10,383,752 B2 | 8/2019 | Shahriari et al. |
| 10,390,930 B2 | 8/2019 | Arbefeuille et al. |
| 10,390,932 B2 | 8/2019 | Lostetter |
| 10,405,964 B2 | 9/2019 | Hannes et al. |
| 10,405,965 B2 | 9/2019 | Kelly |
| 10,405,966 B2 | 9/2019 | Johnson |
| 10,420,637 B2 | 9/2019 | Fierens et al. |
| 10,441,221 B2 | 10/2019 | Spindler |
| 10,463,517 B2 | 11/2019 | Bradway et al. |
| 10,470,868 B2 | 11/2019 | Kim et al. |
| 10,470,870 B2 | 11/2019 | Schreck et al. |
| 10,478,195 B2 | 11/2019 | Aboytes et al. |
| 10,478,320 B2 | 11/2019 | Shahriari |
| 10,485,649 B2 | 11/2019 | Barthold et al. |
| 10,485,684 B2 | 11/2019 | Marmur et al. |
| 10,492,900 B2 | 12/2019 | Kelly |
| 2001/0014794 A1 | 8/2001 | Moll et al. |
| 2001/0018609 A1 | 8/2001 | Smith |
| 2001/0037137 A1 | 11/2001 | Vardi et al. |
| 2001/0049554 A1 | 12/2001 | Ruiz et al. |
| 2002/0115982 A1* | 8/2002 | Barbut ............ A61M 25/0082 604/509 |
| 2002/0183628 A1 | 12/2002 | Reich et al. |
| 2003/0104030 A1 | 6/2003 | Igaki et al. |
| 2003/0139802 A1 | 7/2003 | Wulfman et al. |
| 2003/0139803 A1 | 7/2003 | Sequin et al. |
| 2003/0149472 A1 | 8/2003 | Pinchuk et al. |
| 2003/0195617 A1 | 10/2003 | Schatz |
| 2003/0225453 A1 | 12/2003 | Murch |
| 2004/0093068 A1 | 5/2004 | Bergen et al. |
| 2004/0093078 A1 | 5/2004 | Moll et al. |
| 2004/0098091 A1 | 5/2004 | Erbel et al. |
| 2004/0116998 A1 | 6/2004 | Erbel et al. |
| 2004/0215335 A1 | 10/2004 | Brin et al. |
| 2004/0230295 A1 | 11/2004 | Shaolian et al. |
| 2005/0021133 A1 | 1/2005 | Li |
| 2005/0033405 A1 | 2/2005 | Solovay |
| 2005/0266043 A1 | 12/2005 | Tseng et al. |
| 2006/0030911 A1 | 2/2006 | Letort |
| 2006/0106406 A1 | 5/2006 | Weinberger |
| 2006/0161241 A1 | 7/2006 | Barbut et al. |
| 2006/0206198 A1 | 9/2006 | Churchwell et al. |
| 2006/0212113 A1 | 9/2006 | Shaolian et al. |
| 2006/0253190 A1 | 11/2006 | Kuo |
| 2006/0271163 A1 | 11/2006 | Shokoohi et al. |
| 2006/0271164 A1 | 11/2006 | Shaolian et al. |
| 2006/0009835 A1 | 12/2006 | Osborne et al. |
| 2006/0276883 A1 | 12/2006 | Greenberg et al. |
| 2007/0038288 A1 | 2/2007 | Lye et al. |
| 2007/0118208 A1 | 5/2007 | Kerr |
| 2007/0156228 A1 | 7/2007 | Majercak et al. |
| 2007/0168013 A1 | 7/2007 | Douglas |
| 2007/0173921 A1 | 7/2007 | Wholey et al. |
| 2007/0208410 A1 | 9/2007 | Berra et al. |
| 2007/0282422 A1 | 12/2007 | Biggs et al. |
| 2007/0299497 A1 | 12/2007 | Shaolian et al. |

(56) References Cited

U.S. PATENT DOCUMENTS

| | | |
|---|---|---|
| 2008/0082154 A1 | 4/2008 | Tseng et al. |
| 2008/0097578 A1 | 4/2008 | Erickson et al. |
| 2008/0109055 A1 | 5/2008 | Hlavka et al. |
| 2008/0208312 A1 | 8/2008 | Kwitkin et al. |
| 2008/0208317 A1 | 8/2008 | Jang et al. |
| 2008/0262604 A1 | 10/2008 | Stengel |
| 2009/0030502 A1 | 1/2009 | Sun et al. |
| 2009/0093873 A1 | 4/2009 | Navia |
| 2009/0099652 A1 | 4/2009 | Granada et al. |
| 2009/0164001 A1 | 6/2009 | Biggs et al. |
| 2009/0264993 A1 | 10/2009 | Greenan |
| 2009/0270965 A1 | 10/2009 | Sinha et al. |
| 2010/0087907 A1 | 4/2010 | Lattouf |
| 2010/0174357 A1 | 7/2010 | LeMaitre et al. |
| 2010/0241163 A1 | 9/2010 | Wilcox et al. |
| 2010/0249898 A1 | 9/2010 | Gale et al. |
| 2010/0256728 A1 | 10/2010 | Rea Peterson |
| 2010/0318174 A1 | 12/2010 | Shaolian et al. |
| 2011/0022153 A1* | 1/2011 | Schreck ............... A61F 2/856 623/1.13 |
| 2011/0190867 A1 | 8/2011 | VonderWalde et al. |
| 2011/0196477 A1* | 8/2011 | Ganesan ............... A61F 2/07 623/1.35 |
| 2011/0218608 A1 | 9/2011 | Cheng et al. |
| 2011/0270379 A1 | 11/2011 | Bruszewski |
| 2012/0116500 A1 | 5/2012 | Jang et al. |
| 2012/0191174 A1 | 7/2012 | Vinluan et al. |
| 2012/0316632 A1 | 12/2012 | Gao |
| 2013/0066416 A1 | 3/2013 | Goicoechea et al. |
| 2013/0166015 A1 | 6/2013 | Roeder |
| 2013/0204351 A1 | 8/2013 | Cox et al. |
| 2013/0310922 A1 | 11/2013 | Stengel |
| 2014/0018902 A1 | 1/2014 | Myr |
| 2014/0243952 A1 | 8/2014 | Parodi |
| 2014/0336745 A1 | 11/2014 | Barthold et al. |
| 2015/0012081 A1 | 1/2015 | Robin |
| 2015/0190255 A1 | 7/2015 | Molaei et al. |
| 2016/0030155 A1 | 2/2016 | Cox et al. |
| 2016/0067071 A1 | 3/2016 | Jose et al. |
| 2016/0184076 A1 | 6/2016 | Choubey et al. |
| 2016/0184077 A1 | 6/2016 | Choubey et al. |
| 2016/0184078 A1 | 6/2016 | Choubey et al. |
| 2016/0338823 A1 | 11/2016 | Akingba |
| 2016/0361153 A1 | 12/2016 | Shahriari |
| 2017/0007392 A1 | 1/2017 | Lourenco et al. |
| 2017/0135806 A1 | 5/2017 | Ombrellaro |
| 2017/0216062 A1 | 8/2017 | Armstrong et al. |
| 2017/0296326 A1 | 10/2017 | Chua et al. |
| 2017/0319359 A1 | 11/2017 | Mehta |
| 2017/0333046 A1 | 11/2017 | Roselli |
| 2018/0036111 A1 | 2/2018 | Despalle De Bearn |
| 2018/0098837 A1 | 4/2018 | Shahriari |
| 2018/0125636 A1 | 5/2018 | Kerr |
| 2018/0206972 A1 | 7/2018 | Arbefeuille et al. |
| 2018/0221130 A1 | 8/2018 | Schreck |
| 2018/0243113 A1 | 8/2018 | Walzman |
| 2018/0256189 A1 | 9/2018 | Roeder et al. |
| 2018/0256190 A1 | 9/2018 | Roeder et al. |
| 2018/0303598 A1 | 10/2018 | Szopinski |
| 2019/0029798 A1 | 1/2019 | Walther et al. |
| 2019/0069986 A1* | 3/2019 | Lukas ............... A61F 2/07 |
| 2019/0070026 A1 | 3/2019 | Fulton |
| 2019/0070027 A1 | 3/2019 | Wang et al. |
| 2019/0083227 A1 | 3/2019 | Barone |
| 2019/0105149 A1 | 4/2019 | Roselli et al. |
| 2019/0105150 A1 | 4/2019 | Tsao |
| 2019/0110912 A1 | 4/2019 | Liebig et al. |
| 2019/0133749 A1 | 5/2019 | Liu |
| 2019/0159886 A1 | 5/2019 | Lourenco |
| 2019/0209285 A1 | 7/2019 | Gibbons, Jr. et al. |
| 2019/0231358 A1 | 8/2019 | Henkes et al. |
| 2019/0231513 A1 | 8/2019 | Leuthardt et al. |
| 2019/0239895 A1 | 8/2019 | Dawson et al. |
| 2019/0240049 A1 | 8/2019 | Dawson et al. |
| 2019/0240050 A1 | 8/2019 | Dawson et al. |
| 2019/0247051 A1 | 8/2019 | Siddiqui |
| 2019/0247179 A1 | 8/2019 | Lostetter |
| 2019/0254817 A1 | 8/2019 | Centola et al. |
| 2019/0269497 A1 | 9/2019 | Arbefeuille |
| 2019/0282355 A1 | 9/2019 | Lostetter |
| 2019/0314138 A1 | 10/2019 | O'Brien et al. |
| 2019/0343533 A1 | 11/2019 | Costalat |
| 2019/0365523 A1 | 12/2019 | Haulon et al. |
| 2019/0365524 A1 | 12/2019 | Wilger et al. |
| 2019/0365525 A1 | 12/2019 | Bradway et al. |
| 2019/0374232 A1 | 12/2019 | Lorenzo |
| 2019/0380825 A1 | 12/2019 | Perkins et al. |

FOREIGN PATENT DOCUMENTS

| | | |
|---|---|---|
| EP | 0806191 A1 | 11/1997 |
| EP | 0621016 B1 | 8/1999 |
| EP | 0579523 B1 | 9/2001 |
| EP | 1214021 B1 | 6/2002 |
| EP | 0766539 B1 | 5/2003 |
| EP | 1312320 A2 | 5/2003 |
| EP | 0836449 B1 | 8/2003 |
| EP | 1356788 A2 | 10/2003 |
| EP | 1364626 A1 | 11/2003 |
| EP | 0699424 B1 | 3/2004 |
| EP | 0969778 B1 | 9/2004 |
| EP | 0747020 B1 | 1/2005 |
| EP | 0955954 B1 | 3/2005 |
| EP | 1523999 A1 | 4/2005 |
| EP | 1534177 A2 | 6/2005 |
| EP | 0861638 B1 | 9/2005 |
| EP | 1107708 B1 | 1/2006 |
| EP | 1616585 A1 | 1/2006 |
| EP | 1263348 B1 | 2/2006 |
| EP | 0955017 B1 | 6/2006 |
| EP | 1135082 B1 | 8/2006 |
| EP | 1749545 A2 | 2/2007 |
| EP | 1772115 A1 | 4/2007 |
| EP | 1307162 B1 | 2/2008 |
| EP | 1487380 B1 | 2/2008 |
| EP | 1788977 B1 | 3/2008 |
| EP | 1920734 A2 | 5/2008 |
| EP | 1955680 A1 | 8/2008 |
| EP | 1961401 A2 | 8/2008 |
| EP | 1803418 B1 | 10/2008 |
| EP | 1673037 B1 | 8/2009 |
| EP | 1333787 B1 | 12/2009 |
| EP | 1311208 B1 | 3/2010 |
| EP | 2030592 B1 | 5/2010 |
| EP | 1338252 B1 | 7/2010 |
| EP | 2063812 B1 | 11/2010 |
| EP | 1933763 B1 | 1/2011 |
| EP | 1924220 B1 | 8/2011 |
| EP | 2224880 B1 | 1/2013 |
| EP | 2550943 A1 | 1/2013 |
| EP | 2387379 B1 | 3/2013 |
| EP | 1503701 B1 | 8/2013 |
| EP | 1985258 B1 | 11/2013 |
| EP | 2679197 A1 | 1/2014 |
| EP | 2698126 A1 | 2/2014 |
| EP | 2708208 A2 | 3/2014 |
| EP | 2769701 A1 | 8/2014 |
| EP | 1123063 B1 | 3/2015 |
| EP | 2915509 A1 | 9/2015 |
| EP | 2654629 B1 | 10/2015 |
| EP | 2499997 B1 | 11/2015 |
| EP | 2590602 B1 | 12/2015 |
| EP | 1962722 B1 | 3/2016 |
| EP | 2328512 B1 | 4/2016 |
| EP | 2777609 B1 | 6/2016 |
| EP | 2403439 B1 | 7/2016 |
| EP | 2846733 B1 | 8/2016 |
| EP | 2706954 B1 | 10/2016 |
| EP | 3085339 A1 | 10/2016 |
| EP | 3090707 A1 | 11/2016 |
| EP | 2775958 B1 | 1/2017 |
| EP | 2298248 B1 | 4/2017 |
| EP | 3284439 A1 | 2/2018 |
| EP | 3315092 A2 | 5/2018 |

(56) References Cited

FOREIGN PATENT DOCUMENTS

| | | |
|---|---|---|
| EP | 3326582 A1 | 5/2018 |
| EP | 2846731 B1 | 7/2018 |
| EP | 2999429 B1 | 7/2018 |
| EP | 3003230 B1 | 7/2018 |
| EP | 3351210 A1 | 7/2018 |
| EP | 2543345 B1 | 8/2018 |
| EP | 2967577 B1 | 8/2018 |
| EP | 3391852 A2 | 10/2018 |
| EP | 3395295 A1 | 10/2018 |
| EP | 3395302 A1 | 10/2018 |
| EP | 3395300 A1 | 11/2018 |
| EP | 3421010 A1 | 1/2019 |
| EP | 3431038 A1 | 1/2019 |
| EP | 3431039 A1 | 1/2019 |
| EP | 3443935 A1 | 2/2019 |
| EP | 3248572 B1 | 5/2019 |
| EP | 3197394 B1 | 7/2019 |
| EP | 3524175 A1 | 8/2019 |
| EP | 3539507 A1 | 9/2019 |
| EP | 3244828 B1 | 12/2019 |
| EP | 3253330 B1 | 12/2019 |
| EP | 3578134 A2 | 12/2019 |
| EP | 3578135 A1 | 12/2019 |
| EP | 3578136 A1 | 12/2019 |
| EP | 2806826 B1 | 1/2020 |
| EP | 3060177 B1 | 1/2020 |
| EP | 3397202 B1 | 1/2020 |
| EP | 3323385 B1 | 3/2020 |
| EP | 3448312 B1 | 3/2020 |
| EP | 2811937 B1 | 4/2020 |
| EP | 3448313 B1 | 4/2020 |
| WO | WO 95/03754 A1 | 2/1995 |
| WO | WO 98/15237 A1 | 4/1998 |
| WO | WO 98/22045 A1 | 5/1998 |
| WO | WO 98/41167 A1 | 9/1998 |
| WO | WO 99/51165 A1 | 10/1999 |
| WO | WO 01/21108 A1 | 3/2001 |
| WO | WO 01/39696 A1 | 6/2001 |
| WO | WO 01/93782 A1 | 12/2001 |
| WO | WO 02/00139 A1 | 1/2002 |
| WO | WO 02/22049 A2 | 3/2002 |
| WO | WO 02/43799 A1 | 6/2002 |
| WO | WO 02/087473 A1 | 11/2002 |
| WO | WO 03/007785 A1 | 1/2003 |
| WO | WO 03/039613 A1 | 5/2003 |
| WO | WO 03/086239 A1 | 10/2003 |
| WO | WO 03/099108 A2 | 12/2003 |
| WO | WO 2004/037116 A2 | 5/2004 |
| WO | WO 2004/045452 A2 | 6/2004 |
| WO | WO 2004/096090 A1 | 11/2004 |
| WO | WO 2005/086942 A2 | 9/2005 |
| WO | WO 2005/102221 A1 | 11/2005 |
| WO | WO 2005/112823 A1 | 12/2005 |
| WO | WO 2005/122957 A1 | 12/2005 |
| WO | WO 2006/047184 A2 | 5/2006 |
| WO | WO 2006/067534 A1 | 6/2006 |
| WO | WO 2006/071487 A1 | 7/2006 |
| WO | WO 2006/072835 A2 | 7/2006 |
| WO | WO 2006/072934 A2 | 7/2006 |
| WO | WO 2006/091891 A2 | 8/2006 |
| WO | WO 2006/103641 A1 | 10/2006 |
| WO | WO 2007/028112 A2 | 3/2007 |
| WO | WO 2007/080352 A1 | 7/2007 |
| WO | WO 2007/088549 A2 | 8/2007 |
| WO | WO 2007/112025 A2 | 10/2007 |
| WO | WO 2008/072838 A1 | 6/2008 |
| WO | WO 2008/091925 A2 | 7/2008 |
| WO | WO 2008/157507 A2 | 12/2008 |
| WO | WO 2009/019664 A2 | 2/2009 |
| WO | WO 2009/104000 A1 | 8/2009 |
| WO | WO 2009/140638 A1 | 11/2009 |
| WO | WO 2009/158170 A1 | 12/2009 |
| WO | WO 2010/027363 A1 | 3/2010 |
| WO | WO 2010/027677 A1 | 3/2010 |
| WO | WO 2010/054604 A1 | 5/2010 |
| WO | WO 2010/083558 A1 | 7/2010 |
| WO | WO 2010/111666 A1 | 9/2010 |
| WO | WO 2010/120417 A1 | 10/2010 |
| WO | WO 2011/007354 A1 | 1/2011 |
| WO | WO 2011/023105 A1 | 3/2011 |
| WO | WO 2011/110092 A1 | 9/2011 |
| WO | WO 2012/016886 A2 | 2/2012 |
| WO | WO 2012/061526 A2 | 5/2012 |
| WO | WO 2012/145826 A1 | 11/2012 |
| WO | WO 2012/153069 A1 | 11/2012 |
| WO | WO 2012/159524 A1 | 11/2012 |
| WO | WO 2013/016984 A1 | 2/2013 |
| WO | WO 2013/030819 A1 | 3/2013 |
| WO | WO 2013/097759 A1 | 7/2013 |
| WO | WO 2013/116860 A1 | 8/2013 |
| WO | WO 2013/162682 A1 | 10/2013 |
| WO | WO 2014/028913 A1 | 2/2014 |
| WO | WO 2014/072501 A2 | 5/2014 |
| WO | WO 2014/169267 A1 | 10/2014 |
| WO | WO 2014/180161 A1 | 11/2014 |
| WO | WO 2016/044647 A2 | 3/2016 |
| WO | WO 2016/065208 A1 | 4/2016 |
| WO | WO 2016/075615 A2 | 5/2016 |
| WO | WO 2016/109753 A1 | 7/2016 |
| WO | WO 2016/109757 A1 | 7/2016 |
| WO | WO 2016/122862 A1 | 8/2016 |
| WO | WO 2016/123676 A1 | 8/2016 |
| WO | WO 2016/125137 A1 | 8/2016 |
| WO | WO 2016/191602 A1 | 12/2016 |
| WO | WO 2016/203040 A1 | 12/2016 |
| WO | WO 2016/205826 A1 | 12/2016 |
| WO | WO 2017/040659 A1 | 3/2017 |
| WO | WO 2017/081213 A1 | 5/2017 |
| WO | WO 2017/105479 A1 | 6/2017 |
| WO | WO 2017/134198 A1 | 8/2017 |
| WO | WO 2017/165840 A1 | 9/2017 |
| WO | WO 2017/172735 A1 | 10/2017 |
| WO | WO 2017/205486 A1 | 11/2017 |
| WO | WO 2017191511 | 11/2017 |
| WO | WO 2017/207689 A1 | 12/2017 |
| WO | WO 2017/220400 A1 | 12/2017 |
| WO | WO 2018/007230 A1 | 1/2018 |
| WO | WO 2018/026768 A1 | 2/2018 |
| WO | WO 2018/035167 A1 | 2/2018 |
| WO | WO 2018/045097 A1 | 3/2018 |
| WO | WO 2018/046917 A1 | 3/2018 |
| WO | WO 2018/052878 A1 | 3/2018 |
| WO | WO 2018/060716 A1 | 4/2018 |
| WO | WO 2018/067171 A1 | 4/2018 |
| WO | WO 2018/077499 A1 | 5/2018 |
| WO | WO 2018/077821 A1 | 5/2018 |
| WO | WO 2018/091464 A1 | 5/2018 |
| WO | WO 2018/095090 A1 | 5/2018 |
| WO | WO 2018/106573 A1 | 6/2018 |
| WO | WO 2018/163056 A1 | 9/2018 |
| WO | WO 2018/173056 A1 | 9/2018 |
| WO | WO 2018/200972 A1 | 11/2018 |
| WO | WO 2019/010458 A1 | 1/2019 |
| WO | WO 2019/012123 A1 | 1/2019 |
| WO | WO 2019/048551 A1 | 3/2019 |
| WO | WO 2019/059949 A2 | 3/2019 |
| WO | WO 2019/072912 A1 | 4/2019 |
| WO | WO 2019/084951 A1 | 5/2019 |
| WO | WO 2019/085981 A1 | 5/2019 |
| WO | WO 2019/097328 A1 | 5/2019 |
| WO | WO 2019/101077 A1 | 5/2019 |
| WO | WO 2019/101078 A1 | 5/2019 |
| WO | WO 2019/101079 A1 | 5/2019 |
| WO | WO 2019/122665 A1 | 6/2019 |
| WO | WO 2019/122944 A1 | 6/2019 |
| WO | WO 2019/126060 A1 | 6/2019 |
| WO | WO 2019/128775 A1 | 7/2019 |
| WO | WO 2019/144870 A1 | 8/2019 |
| WO | WO 2019/174991 A1 | 9/2019 |
| WO | WO 2019/188345 A1 | 10/2019 |
| WO | WO 2019/205599 A1 | 10/2019 |

\* cited by examiner

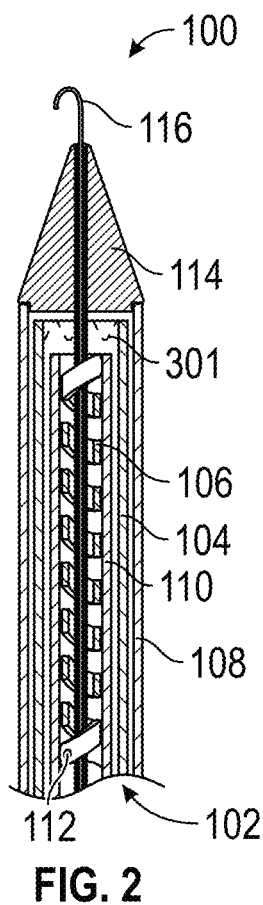 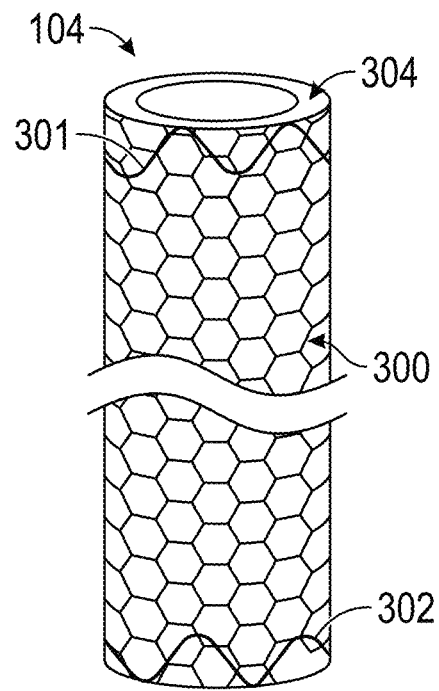 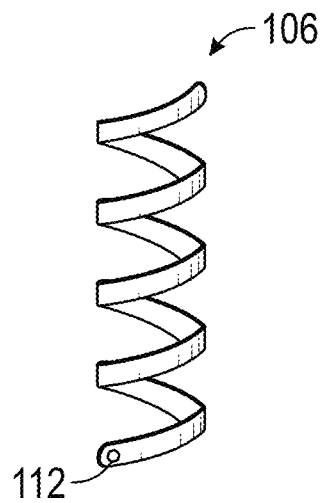
FIG. 2
FIG. 3
FIG. 4

AORTIC DISSECTION IMPLANT

INCORPORATION BY REFERENCE TO ANY PRIORITY APPLICATIONS

This application claims the benefit of U.S. Provisional Application No. 62/821,052, filed Mar. 20, 2019, the entirety of which is hereby incorporated by reference.

BACKGROUND OF THE INVENTION

Field of the Invention

The present disclosure generally relates to implantable medical devices and, more particularly, to aortic dissection implants, systems for their delivery, and their methods of use.

Description of the Related Art

Acute Aortic Dissections occur when a portion of the aortic intima (the inner most layer of the aorta) ruptures and systemic blood pressure serves to delaminate the intimal layer from the media layer resulting in a false lumen for blood flow that can propagate in multiple directions along the length of the aorta. AAD's impact approximately 7,000 patients in the US annually and are the most common catastrophe of the aorta, carrying very high mortality rates. Dissections that occur in the ascending portion of the aorta make up the majority of cases (63%) and are referred to as Type A, while those occurring in the descending aorta are called Type B. Although Type B AAD's can sometimes be managed medically, Type A dissections typically require immediate surgery. With mortality rates of 1-2% per hour, 25% of patients die within the first 24 to 48 hours, and 80% die within two weeks of diagnosis.

FIGS. 1A-1F illustrates various Types of Acute Aortic Dissections (AADs) that may be referred to herein. Despite the high mortality associated with Type A dissections (FIG. 1A), a need remains for options to treat Type A dissections percutaneously. One option for treating Type A dissections includes a single-piece implant constructed of fabric with built-in reinforcement that resides only in the ascending aorta. However, the shorter length of the implant compromises stability and this option does not address the downstream aspects of the head vessels and the initial portion of the descending aorta. Another option for treatment addresses the downstream portions with a bare-metal implant (no fabric) after the initial dissection in the ascending aorta is treated surgically. In this option, while the reinforcement need is addressed, a complete percutaneous solution is not provided. In some scenarios, attempts to treat a dissection with only a bare metal frame can be attempted, but with the risk that the frame can erode through the tissue or cause the fragile intima layer to dissect further.

Aortic grafts for treating aortic aneurysms may incorporate non-porous graft materials that seek to wall off the aneurysm from the main lumen of the graft and the aorta. Consequently, these grafts can be inappropriate for environments with branch vessels that require fenestration windows and/or other modification. As a result, attempting to apply aortic grafts designed for aneurysms to Type A dissections can be cumbersome or simply impossible. Accordingly, there exists an unmet clinical need for a less invasive, non-surgical solution to treat Type A AADs. There also remains a need for improved treatment for other types of Aortic Dissections, such as shown in FIGS. 1B-1F, as described further herein.

SUMMARY OF THE INVENTION

In some aspects of the disclosure, an aortic dissection system for treating a dissection within an aorta of a patient is disclosed. The aortic dissection system may comprise an aortic dissection implant and a delivery system. The aortic dissection implant may comprise an expandable support structure and at least one layer. The expandable support structure may have a proximal end and a distal end. The at least on layer may be provided over the expandable support structure and comprise an atraumatic outer surface configured to engage an inner wall of the aorta adjacent a false lumen associated with the dissection. The delivery system may be configured to be inserted percutaneously into the patient and advanced into the patient's aorta. The delivery system may comprise an outer sheath configured to receive the aortic dissection implant therein in a compressed configuration.

In some aspects, the at least one layer may comprise a non-porous section configured to extend across at least a portion of the dissection.

In some aspects, the at least one layer may comprise a porous layer provided over the expandable support structure and a non-porous layer provided over the porous layer.

In some aspects, the expandable support structure may be configured to extend from the descending aorta, through the aortic arch and into the ascending aorta. The at least one layer may comprise a porous section configured to permit blood flow from within the expandable support structure, through the porous section, and into the carotid arteries and the subclavian arteries. The at least one layer may comprise a non-porous section comprising an opening to allow blood to flow from within the expandable support structure, through the opening, and into the carotid and the subclavian arteries. The expandable support structure may be preformed with a curvature to conform to the aortic arch. The at least one layer may comprise a porous layer configured to substantially cover the expandable support structure from the descending aorta to the sinotubular junction and a non-porous layer partially covering the porous layer and configured to engage a wall of the ascending aorta on opposite sides of a tear of the dissection.

In some aspects, the expandable support structure can be configured to apply radial force to the descending aorta when expanded.

In some aspects, the aortic dissection implant can further comprise an expandable interface structure that may be configured to expand within the aortic root. The expandable interface structure can be configured to extend within the left and right coronary sinuses and distally past the left and right coronary ostia. The expandable interface structure can comprise a wire frame having three lobes. The at least one layer can extend over the expandable support structure and the expandable interface structure. The at least one layer can be configured to extend within the left and right coronary sinuses without blocking blood flow into the left and right coronary arteries.

In some aspects, the at least one layer can comprise a non-porous layer that may be configured to be positioned across at least a portion of the dissection and inflate with blood flow against the inner wall of the aorta adjacent the false lumen. The aortic dissection implant may further comprise at least one valve that can allow blood to enter a space within the non-porous layer but prevent blood from exiting the space.

In some aspects, the delivery system may be configured to sequentially deploy the at least one layer before the expandable support structure.

In some aspects, the system may further comprise one or more temporary longitudinal ribs that can be configured to be removable from the aortic dissection implant. The one or more temporary longitudinal ribs may be configured to maintain a circumferential space between the atraumatic outer surface of the at least one layer and the inner wall of the aorta.

In some aspects, the system can further comprise a temporary external coil that can be configured to surround the aortic dissection implant to maintain a circumferential space between the atraumatic outer surface of the at least one layer and the inner wall of the aorta.

In some aspects, the system can further comprise a suction port along the at least one layer. The suction port may be configured to apply vacuum to a circumferential space between the atraumatic outer surface of the at least one layer and the inner wall of the aorta when a vacuum applicator is applied to the suction port.

In some aspects of the disclosure, an aortic dissection implant for treating a dissection within an aorta of a patient is provided having the features described above and/or as described further below. Any of the aortic dissection implants as described above or as described further herein may comprise an expandable anchoring structure and an elongate tubular structure. The expandable anchoring structure may be configured to be positioned within the aortic root of a patient and apply radial force to one or more of the sinuses of the aortic root and/or the sinotubular junction when expanded. The elongate tubular structure can have a proximal end and a distal end. The proximal end of the elongate tubular structure may be configured to be positioned in the descending aorta. The distal end of the elongate tubular structure can be configured to be positioned in the ascending aorta, the sinotubular junction, or the aortic root. The expandable anchoring structure can be connected to or forms the distal end of the elongate tubular structure. The elongate tubular structure can comprises an expandable support frame, a first porous layer, and a second porous layer. The expandable support frame may have a first length configured to extend from the descending aorta to at least the ascending aorta and curve along with a curvature of the aortic arch when expanded within the aorta. The first porous layer may be positioned over the expandable support frame and may have a second length configured to extend from the descending aorta at least partially through the aortic arch. The first porous layer may comprise an atraumatic outer surface. Expansion of the expandable support frame when positioned within the aorta may expand the first porous layer such that the atraumatic outer surface of the first porous layer presses against an interior surface of the aorta and applies a radial force at least to the descending aorta. The second non-porous layer may be positioned over the expandable support frame and may have a third length that is less than the first length. The second non-porous layer can comprise a first end and a second end that can be configured to be positioned on opposite sides of a tear of the dissection. The second non-porous layer can be inflatable when in use via blood flow through at least the expandable support frame to cause the non-porous layer to expand and seal against at least a portion of the dissection.

The aortic dissection implant of any of the preceding paragraphs or as described further herein can also include one or more of the following features. The second length of the first porous layer can be approximately the same as the first length of the expandable support frame. One or both of the first porous layer and the second non-porous layer can comprise a fabric material. The expandable support frame can comprise a wire, a coiled ribbon, a laser cut structure, or a braid. The atraumatic outer surface of the first porous layer can be configured to engage an interior surface of the aorta within the aortic arch and to allow blood flow from the aortic arch, through the first porous layer, and to the carotid and/or subclavian arteries. The expandable anchoring structure can comprise openings for allowing blood flow to the left and right coronary ostia. The expandable support frame can have a tubular shape when expanded and the expandable anchoring structure can have a cross-sectional dimension larger than a cross-section dimension of the expandable support frame when expanded. The expandable anchoring structure can comprise a trilobe shape. The second non-porous layer can be configured to be positioned over the expandable support frame within the ascending aorta.

In some aspects, the aortic dissection implant of any of the preceding paragraphs or as described further herein can further comprise a third layer between the first layer and the second layer. The third layer can provide for a one-way valve configured to allow blood to enter a space between the first layer and the second layer and prevent blood from exiting the space.

In some aspects of the disclosure, an aortic dissection implant for treating a dissection within an aorta of a patient is provided that comprises a proximal end, a distal end, an expandable support structure, at least one layer, and an expandable interface portion. The proximal end may be configured to be positioned within the descending aorta and the distal end may be configured to be positioned within an aortic root of the patient. The expandable support structure can be configured to extend from the descending aorta to the ascending aorta and curve along with a curvature of the aortic arch when expanded within the aorta. The at least one layer can be provided over the support structure. The at least one layer can comprise a porous section and a non-porous section. The porous section can be configured to curve along with the curvature of the aortic arch and allow blood to flow into the carotid and subclavian arteries of the patient. The non-porous section can be configured to engage a wall of the aorta on opposite sides of a tear in the aorta associated with the dissection. The expandable interface portion at the distal end of the aortic dissection implant can be configured to expand into contact with the aortic root.

The aortic dissection implant of any of the preceding paragraphs or as described further herein can also include one or more of the following features. The expandable support structure may comprise a coiled wire, a coiled ribbon, a laser cut structure, or a braid. The expandable support structure may be formed from one or more of a metal, a polymer, a biological material and a bio-absorbable material. The expandable support structure may comprise a tubular wire frame. the at least one layer may comprise a single layer having variable porosity. The at least one layer may comprise a tubular fabric layer. The at least one layer may comprise a tubular layer that may have radial support features at proximal and distal ends thereof. The expandable interface portion may be contiguous with the at least one layer. The expandable interface portion may be configured to extend within the left and right coronary sinuses and distally past the left and right coronary ostia. The expandable interface portion may comprise openings for allowing blood flow to the left and right coronary ostia. The expandable interface portion may comprise a wire frame having three lobes. The expandable support structure may be a separate structure from the expandable interface portion. The expandable support structure may be connected to the expandable interface portion by the at least one layer. The expandable support structure and the expandable interface portion may be formed from a single wire. The at least one layer may comprise a porous layer that may be configured to substantially cover the expandable support structure from the descending aorta to the sinotubular junction and a non-porous layer that may partially cover the porous layer and may be configured to engage a wall of the aorta on opposite sides of a tear of the dissection. The system may further comprise an expandable portion that may be proximal to the expandable interface portion. The expandable portion may be configured to radially expand against the sinotubular junction.

In some aspects, a method of treating a dissection with an aorta of a patient is disclosed. The method can comprise: delivering an aortic dissection implant in a collapsed configuration percutaneously into a patient to a treatment location within the aorta; and expanding the aortic dissection implant to an expanded configuration within the aorta. After expansion of the aortic dissection implant, a non-porous section of the aortic dissection implant can engage an inner wall of the aorta on opposite sides of a tear of the dissection.

The method of the preceding paragraph or as described further herein can also include one or more of the following features. The aortic dissection implant can comprise a portion that can be expanded within the descending aorta and can apply a radial force at least to the descending aorta. The aortic dissection implant can comprise a portion that can be expanded within the aortic root and can apply a radial force to one or both of the aortic root and the sinotubular junction. After expansion, a porous section of the aortic dissection implant can cover openings to the carotid and subclavian arteries to allow blood flow therethrough. After expansion, a porous section of the aortic dissection implant can cover one or both of the left and right coronary ostia to allow blood flow therethrough. The method can further comprise inflating the non-porous section with blood flow to expand the non-porous layer against the inner wall of the aorta. The method can further comprise reducing a false lumen in the aorta by drawing fluid from the false lumen through natural fenestrations of the aorta.

In some aspects, a dual-layer implant for a blood vessel is disclosed that comprises a first implant layer and a second implant layer. The first implant layer may have an atraumatic outer surface and a first resting diameter. The second implant layer, may be separate from the first implant layer, and may have a second resting diameter that is greater than the first resting diameter. The second implant layer may be configured to be disposed interior to the first implant layer and to expand the first implant layer such that the atraumatic outer surface of the first implant layer presses against a surface of the blood vessel.

The dual-layer implant of the preceding paragraph can also include one or more of the following features. The first implant layer can be a tubular layer having a central lumen that can be configured to receive the second implant layer and to coincide with a true lumen of the blood vessel. The first implant layer can be a fabric layer. The second implant layer can comprise a coil. The coil can be a metal coil. The metal coil can comprise a coil retention feature that can be configured to engage with a coil retention structure of a delivery system and to release from the coil retention structure upon implantation of the second implant layer. The first implant layer and the second implant layer can be bendable to conform to an aortic arch. The first implant layer can include at least a portion that is porous to allow blood flow from the aortic arch, through the first implant layer, to the carotid or subclavian arteries. The dual-layer implant may further comprise an interface structure for interfacing with the native anatomy of the aortic valve cusps. The interface structure may include fenestrations for allowing blood flow to the left and right coronary ostia. The first implant layer may further comprise a non-porous portion and at least one temporary rib. The dual-layer implant may further comprise at least a portion that is radiopaque. The dual-layer implant may further comprise at least a portion that is echogenic. The first implant layer may comprise radial support structures at opposing ends thereof.

In some aspects, a system is disclosed that comprises the dual-layer implant of any one of the preceding paragraphs and a delivery system. The delivery system can be configured to deliver the first implant layer and the second implant layer together into the blood vessel.

In some aspects, a system is disclosed that comprises the dual-layer implant of any one of the preceding paragraphs and a delivery system. The delivery system may be configured to decouple the first implant layer and the second implant layer for asynchronous deployment and release into the blood vessel.

In some aspects, a method of implanting a dual-layer implant is disclosed. The method can comprise: inserting the implant percutaneously into the femoral artery of a patient and advancing the implant into the patient's aorta; retracting an outer sheath to deploy a first implant layer and allow the first implant layer to radially expand to a first resting diameter within the aorta; manipulating a retention structure to deploy a second implant layer, within a lumen of the first implant layer, from the retention structure; further manipulating the retention structure to cause the second implant layer to radially expand to a second resting diameter that is greater than the first resting diameter to cause the first implant layer to radially expand beyond the first resting diameter into contact with the aorta.

The method of the preceding paragraph can also include one or more of the following features. Retracting the outer sheath may deploy deployment arms that may cause the first implant layer to radially expand, and wherein the method further comprising, removing the deployment arms after deployment of the second implant layer. The dual-layer implant may include any of the features of any of the preceding paragraphs. The first implant layer may further comprise a radial support feature at a distal end or a proximal end. The method may further comprise: maintaining, with longitudinal support ribs coupled to the first implant layer, a space between an outer surface of the first implant layer and an interior wall of the aorta; and applying a vacuum to a channel that extends from an inner surface of the first implant layer to the outer surface of the first implant layer to reduce a false lumen in the aorta by drawing fluid from the false lumen through natural fenestrations of the aorta. The method may further comprise removing the longitudinal support ribs.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments.

FIG. 2 is a schematic partial cross-sectional view of an aortic dissection graft system loaded inside a delivery system according to certain aspects of the present disclosure.

FIG. 3 is a schematic perspective view of a graft component of an aortic dissection system according to certain aspects of the present disclosure.

FIG. 4 is a schematic perspective view of a support member of an aortic dissection system according to certain aspects of the present disclosure.

DETAILED DESCRIPTION OF THE PREFERRED EMBODIMENTS

Figure 1A:
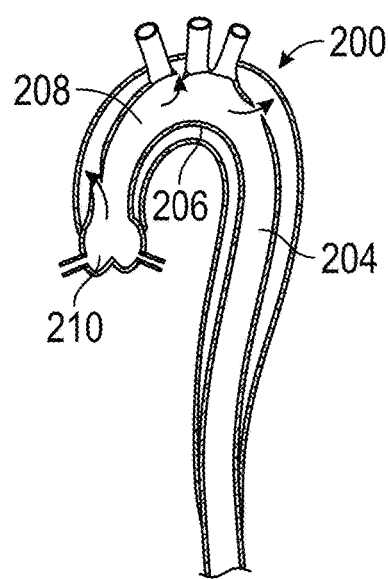
FIGS. 1A-1B show the common classifications of Aortic Dissections: Stanford Type A and B.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Aspects of the subject disclosure are directed to aortic dissection implants, such as dual layer implants, that may be utilized in the treatment of aortic dissections, as well as systems and methods involving the same. In accordance with certain aspects of the subject disclosure, a dual-layer implant is provided that can be used for treatment of Type A Acute Aortic Dissections (AADs), or any other abdominal or thoracic aortic dissection, rupture, or aneurysm. The dual-layer implant can include a first implant layer that forms a soft, atraumatic outer layer to directly contact the intima of the aorta. The dual-layer implant can also include a second implant layer, which can be deployed after or in sequence with the first layer, and that provides reinforcement and direct apposition of the first layer against the intima. Because the first implant layer (e.g., a graft layer) and the second implant layer (e.g., a support structure) in some aspects are not attached together prior to delivery, and can thus be delivered in two separate and/or overlapping steps, the dual-layer implant is sometimes described herein as a dual-layer asynchronous implant. That is, the delivery system for the dual-layer implant, as described in further detail hereinafter, can deploy the two layers together, or can decouple the two layers to allow for asynchronous deployment and release. It will be appreciated that the dual-layer implant as described herein may also be manufactured with the first implant layer provided over the second implant layer, such that the two layers are delivered to a treatment location as a single unit.

FIGS. 2-4 illustrate an aortic dissection implant 102 for use in an aortic dissection system 100 according to certain aspects. The aortic dissection implant 102 can comprise a first implant layer 104, such as a porous and/or non-porous material as described further herein, that may be reinforced with a second implant layer 106, such as a coil, braid, wire frame, Z-stent or any other reinforcement structure as described herein. As used herein, non-porous refers to any material or structure with no openings or openings sufficiently small to prevent blood flow within the ranges of physiological pressures. The aortic dissection system 100 may comprise the aortic dissection implant 102, and a delivery system which may include an outer sheath 108 and/or one or more other delivery components. FIG. 2 illustrates a system 100 including a dual-layer implant 102 packaged for implantation within an outer sheath 108 coupled to a nose cone 114 and mounted to or delivered over a guidewire 116. System 100 is shown in partial cross section in FIG. 2, so that the first implant layer 104 and the second implant layer 106 can be seen. As described in further detail hereinafter, in the delivery configuration shown in FIG. 2, first implant layer 104 and second implant layer 106 are compressed within outer sheath 108 for implantation. Outer sheath 108 can be retracted relative to first implant layer 104 for deployment of first implant layer 104. FIG. 2 also illustrates a retention layer or catheter 110 for second implant layer 106, illustrated in this embodiment as a coil. Retention layer or catheter 110 constrains second implant layer 106 in the compressed configuration of FIG. 2 and is manipulable (e.g., rotatable, retractable or otherwise) for controlled deployment of second implant layer 106. In various examples, dual-layer implant 102 is described herein for treatment of Type A dissections. However, it should be appreciated that dual-layer implant 102 can be applied to Type B dissections and all types of aortic aneurysms as well. It should also be appreciated that in other implementations, implant 102 may comprise more than two layers (e.g. with a secondary graft layer 104 inside of support layer 106 or a secondary support layer inside of support layer 106).

It has been discovered that it is not necessary to "wall-off" the dissected area in the case of AADs, as long as the layers at the source of the dissection can be re-approximated along its length in order to prevent pressure from propagating through the false lumen and to instead direct that pressure through the true lumen. In fact, providing a first implant layer 104 formed from a porous material allows several advantages during deployment (e.g. by not obstructing blood flow), allows for healthier functionality of the aorta, and offers the ability to more easily deal with branch vessels that may be encountered. It is also understood that the aortas in patients with the conditions described herein are very fragile so care must be given in some aspects to make the implant as atraumatic as possible. In some aspects, separating the implant 102 into a soft, atraumatic first layer 104 with a secondary reinforcement layer 106 that is controllably and sequentially deployed asynchronously against the first layer 104 (e.g., after the first layer is in place or prior to the first layer 104 being fully deployed), helps to improve safety. While the native aorta provides its support from the outermost layer, the implant 102 provides support from the inner-most layer 106 with the softer layer 104 on the outside to appose the soft intima layer of the native aorta.

System 100, initially in the configuration shown in FIG. 2, can be inserted percutaneously into the femoral artery and advanced into the patient's aorta 200. As shown in FIGS. 1A-1F, depending on the desired location of treatment and implantation, the system 100 may be advanced from one of the iliac arteries 202 to the descending aorta 204, and may continue around the aortic arch 206, to the ascending aorta 208, and into the aortic root 210. As used herein, the proximal end of the implant 102 or the system 100 is the end closest to the operator and farthest from the aortic root 210, and the distal end of the implant 102 and the system 100 is the end farthest from the operator and closest to the aortic root 210.

In the delivery configuration of FIG. 2, initial outer layer 104 is retained within outer sheath 108, while the reinforcement layer 106 is retained under torsional tension with a mechanism (e.g., by coil retention structure 110) that is arranged to be unwound or unthreaded to allow the secondary implant layer 106 to deploy. Other mechanisms could be utilized to maintain the reduced diameter of each layer during delivery and allow for controlled diametric expansion upon deployment. For example, second implant layer 106 can be alternatively constrained within an inner sheath that can be retracted linearly for deployment of second implant layer 106. Locking mechanism 112 is provided to maintain connection with the delivery system and allow for repositioning, recapturing and/or removal of implant 102, if needed, prior to full deployment of the implant.

FIG. 3 illustrates a perspective view of one example of first implant layer 104, in accordance with aspects of the disclosure. First implant layer 104 can be formed from fabric, metal, polymer or a biological tissue (as examples). First implant layer 104 is sized such that it is capable of reaching a diameter just slightly beyond that of the native aorta (e.g., a maximum diameter of about 40 to 45 mm) when fully expanded with the reinforcement layer 106 inside. In some aspects, first implant layer 104 can have a resting diameter of 30 mm (or about 30 mm), and may be stretchable or can expand (e.g., by second implant layer 106) to an expanded diameter of 40 mm (or about 40 mm) to 45 mm (or about 45 mm). First implant layer 104 may include one or more porous regions 300 that allows for blood to flow through that region (e.g., if the porous region is deployed across the ostia of a branch vessel). The material of first implant layer 104 may be flexible enough to accommodate the curvature of the aortic arch. In some implementations, the entire length of first implant layer 104 could be porous. In other implementations, the entire length of first implant layer 104 may be non-porous. In still other implementations, the level of porosity may vary throughout the length of first implant layer 104. In still other embodiments where 104 has a given thickness, the porosity of the inner surface may differ from the porosity along the outer surface.

First implant layer 104 may be formed from a fabric that is woven in an open honey-comb shape (as shown in FIG. 3) or in one or more other configurations that afford a wall thickness 304, such that the outer diameter of layer 104 can be disposed against the inside of the aorta, and the inner diameter can be compressed against the outer diameter when the inner reinforcement layer 106 is expanded inside layer 104, to distribute the radial load and avoid putting excessive pressure on the aortic wall.

For example, in other embodiments first implant layer 104 may be formed with an open woven pattern, a laser cut pattern, a braided configuration, or any other form that allows for blood to flow through one or more porous portions 300. In some cases, the porosity of first implant layer 104 varies around the circumference and/or along the length of the first implant layer 104 to achieve targeted levels of porosity against different portions of the patient's anatomy. For example, the porosity of the material itself can vary with position on layer 104, or holes, openings, or other fenestrations can be formed in the material of layer 104.

Additionally, the first implant layer 104 or portions of the first implant layer 104 may be formed of a fabric or polymer that is porous and/or non-porous. The first implant layer 104 could comprise one of or a combination of polyester, nylon, polytetrafluoroethylene (PTFE), or silicone.

In the example of FIG. 3, first implant layer 104 includes radial support features 301 and 302, respectively at its distal and proximal ends. Radial support features 301 and 302 may have a radial compressibility that is less than the radial compressibility of the intervening length of first implant layer 104. Radial support features such as radial support features 301 or 302 can be provided to help secure the position of first implant layer 104 prior to the deployment of second implant layer 106. Radial support features 301 and/or 302, and/or other portions of implant 102 may be radiopaque and/or echogenic so as to allow visualization under fluoroscopy and/or ultrasound intra-procedurally. Radial support features may be provided on an outer surface, an inner surface, or embedded within the implant layer 104. Examples of radial support features include wire frames, coils, braids, and stents have a Z-shape, zig-zag pattern, or more complex geometries, e.g., laser cut from a self-expanding shape memory alloy. Radial support features may have a cylindrical shape, a frustoconical shape or other shapes.

As described in further detail hereinafter (see, e.g., FIGS. 8-10 and the associated description), in some implementations, the distal shape (e.g., including radial support feature 301) of first implant layer 104 (or one or more additional interface structures at the distal end of first implant layer 104) may be arranged to interface with the native anatomy of the aortic valve cusps and left and right coronary ostia, in circumstances in which it is desirable to engage as deep as possible within the aortic root without impacting aortic valve function and without obstructing flow to the coronaries. As used herein, aortic valve cusps are intended to include the sinuses of the aortic root. In some implementations, the distal end of the implant may incorporate a prosthetic aortic heart valve (e.g., coupled to or configured to interface with first implant layer 104).

Second implant layer 106 is a reinforcement layer that provides hoop strength and radial force beyond that of the first implant layer 104, and serves to enhance the apposition of the first implant layer 104 against the intima. Second implant layer 106 may be formed from one or more of a metal (e.g., stainless steel, nitinol, or the like), a polymer, a biological material, a bio-absorbable material, and/or other suitable materials. FIG. 4 shows a perspective view of second implant layer 106, in one implementation. Second implant layer 106 may be a coiled wire forming a wire frame, a coiled ribbon as in the example of FIG. 4, a laser cut structure, a braid or may be formed in another open configuration that can accommodate the curvature of the native aorta. Second implant layer 106 may be completely or partially radiopaque and/or echogenic to enhance visualization intra-procedurally.

FIG. 4 illustrates a perspective view of the second implant layer 106. The second implant layer 106, for example, may be formed as a coiled structure having a pitch of approximately 2 cm, an overall length of between approximately 12-15 cm, a cross-sectional width of approximately 0.5 mm, and a resting diameter of approximately 40 mm to approximately 45 mm. Second implant layer 106 may be radially compressible (e.g., by a compressive force from a portion of the aorta) to a diameter of approximately 30 mm. As illustrated in FIG. 2, second implant layer 106 may also be twisted to a further reduced insertion diameter by coil retention structure 110. In the example of FIG. 4, second implant layer 106 is formed from a coiled ribbon having a cross-sectional height of approximately 5 mm.

FIG. 4 also shows a proximal release feature 400 for second implant layer 106. In the example of FIG. 4, proximal release feature 400 is an opening at the proximal end of second implant layer 106. When twisted into the insertion diameter within coil retention structure 110, proximal release feature 400 may be engaged with a corresponding feature on the interior of coil retention structure 110 (e.g., to prevent rotation of the proximal end of second implant layer within coil retention structure 110 while the proximal end is within coil retention structure 110). As described in further detail in connection with FIG. 5, proximal release feature 400 may disengage from the corresponding feature on the interior of coil retention structure 110 as the proximal end of second implant layer 106 exits coil retention structure 110 to complete the implantation of implant 102. Although second implant layer 106 is depicted in FIG. 4 as a single coil, in other implementations, second implant layer 106 may be implemented as double-coil (e.g., with a parallel pitch or an opposite pitch to form a helix) to provide additional support with opposite pitch to form a helix. In still other implementations, second implant layer 106 can be formed by a coarse braid with multi-fillar construction, a single or multiple piece wire form structure, or a laser cut structure.

Figure 5:
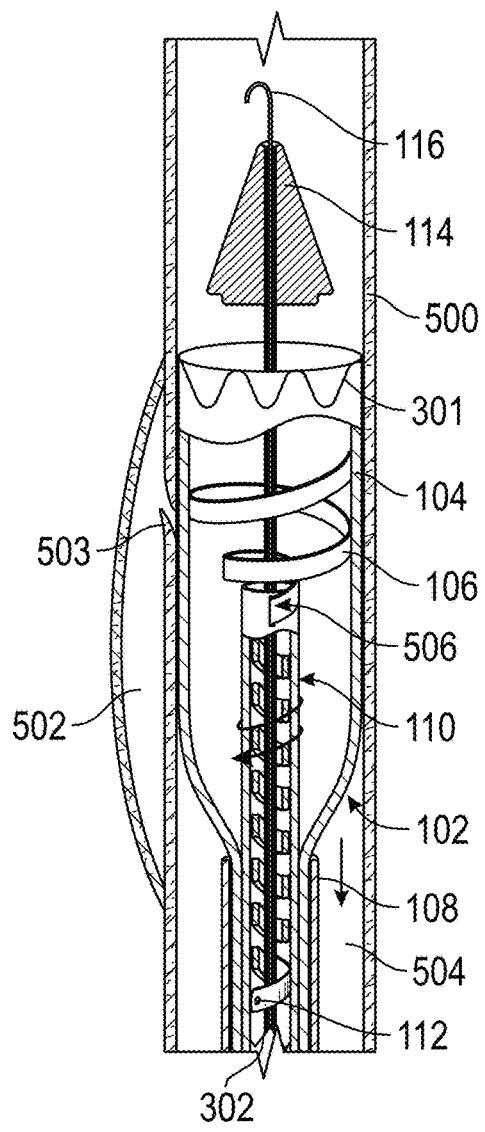
FIG. 5 is another schematic partial cross-sectional view of the aortic dissection system as it is deployed from a delivery system according to certain aspects of the present disclosure.

FIG. 5 illustrates a perspective and partial cross-sectional view of implant 102 (in partial cross-section for clarity) midway through implantation in the true lumen 504 of a blood vessel 500 having a false lumen 502 associated with a dissection 503. The dissection 503 can have an entry tear and may have one or more re-entry tears. In the configuration of FIG. 5, outer sheath 108 has been partially retracted to allow the first implant layer 104 to expand to its resting diameter within true lumen 504 such that the distal end of first implant layer 104 (and distal radial support feature 301) is distal to the dissection 503 and the proximal end of first implant layer 104 is proximal to dissection 503. In the configuration of FIG. 5, coil retention structure 110 has also been rotated to cause a distal portion of second implant layer 106 to exit an opening 506 at the distal end of coil retention structure 110 to begin to expand to its resting diameter at which second implant layer 106 presses first implant layer 104 against the intima of blood vessel 500. In other embodiments, the retention structure 110 may simply be withdrawn as a sheath in order to expose the second implant layer 106 and allow for its expansion.

From the configuration of FIG. 5, implantation of implant 102 can be completed by further withdrawing outer sheath 108 beyond the proximal end of first implant layer 104 to allow radial support feature 302 to exit the sheath and expand to its resting diameter, and further twisting coil retention structure 110 until second implant layer 106 fully exits through opening 506 (and coil retention feature 400 releases from the corresponding internal feature of coil retention structure 110). Locking features 112 may prevent second implant layer 106 from pulling or sliding proximally on first implant layer 102 during deployment of second implant layer 106.

In this way, deployment of the outer layer 104 is initiated first while maintaining the ability to recapture layer 104 up to any point prior to full release. In implementations in which the material of layer 104 is porous, blood pressure collecting inside the implant is avoided, and the deployment of implant 102 can proceed at a measured pace. Once the distal end of the outer implant layer 104 has been expanded, the user has the option to continue to deploy the outer layer 104 or begin to release a portion of the reinforcement layer 106, to further stabilize the position of the first layer 104. If desired, the majority of outer layer 104 may be released from sheath 108 before the deployment of the reinforcement layer 106 is initiated.

At the beginning of deployment of second implant layer 106, the coil retention structure 110 may be twisted such that a distal portion of second implant layer 106 can emerge from opening 506. After continued rotation of coil retention structure 110, the majority of second implant layer 106 can emerge from coil retention structure 110.

Figure 6:
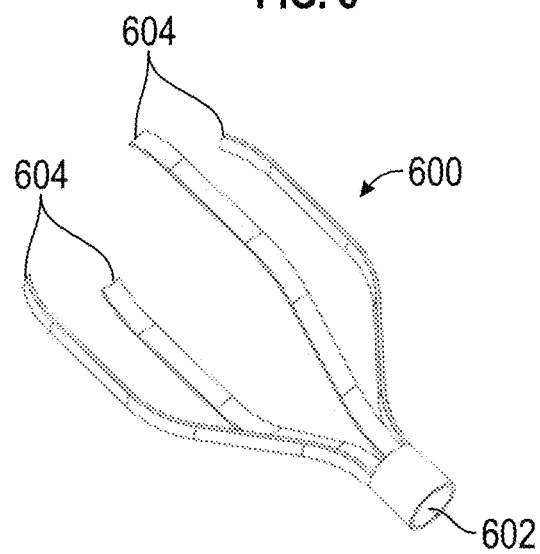
FIG. 6 is a schematic perspective view of delivery support arms for an aortic dissection system according to certain aspects of the present disclosure.

In some implementations, system 100 may include delivery support arms between the initial graft layer 104 and the secondary support layer 106 during delivery. FIG. 6 illustrates a perspective view of example delivery support arms 604, showing four arms. Any number of arms may be provided, such as three or more arms. In order to temporarily expand the graft layer 104 and provide apposition against the intima of the aorta prior to the expansion and secondary support layer 106 to ensure desired location and effect, delivery support arms 604 can be provided in system 100. As shown in FIG. 6, multiple angularly separated delivery support arms 604 may extend from a common base 602 of a delivery support structure 600.

Figure 7:
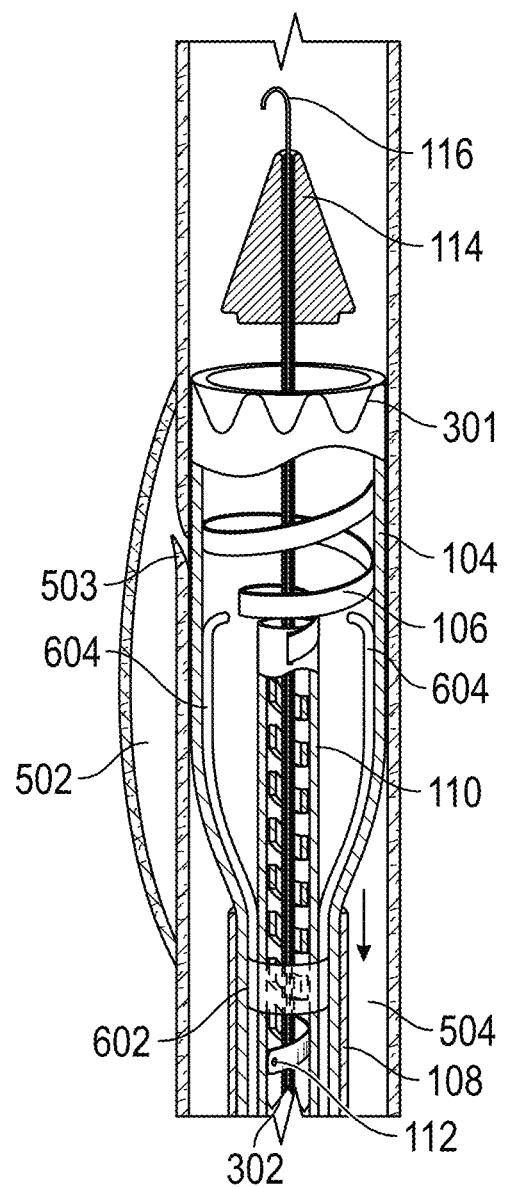
FIG. 7 is another schematic partial cross-sectional view of an aortic dissection system with delivery support arms as the system is deployed from a delivery system according to certain aspects of the present disclosure.

FIG. 7 illustrates system 100, in the delivery state of FIG. 5, in a configuration in which system 100 includes delivery support arms 604. Only two delivery support arms 604 are shown for clarity. As illustrated in FIG. 7, delivery support arms 604 are configured to expand without external assistance as an outer sheath 108 is withdrawn. Base 602 may be coupled to locking mechanism 112 and/or other portions of the delivery system such that delivery support arms 604 move proximally as the delivery sequence progresses (e.g., during deployment of second implant layer 106). Upon full release of both implant layers 104 and 106, outer sheath 108 is advanced interior to the two deployed layers, in order to recapture the delivery support arms for removal. In the example of FIG. 7, delivery support arms 604 extend to the end of first implant layer 104. However, delivery support arms 604 can be provided that are shorter than the distalmost end of second implant layer 106. This arrangement of delivery support arms 604 can help ensure that delivery support arms 604 are not captured between second implant layer 106 and first implant layer 104 when second implant layer 106 is deployed.

FIGS. 5 and 7 illustrate, simply for convenience, deployment of implant 102 in a substantially straight portion of blood vessel 500. However, it should be appreciated that first implant layer 104 and second implant layer 106 as described allow implant 102 to be deployed in curved portions of a blood vessel, and/or in portions of a blood vessel having a varying size.

Figure 8:
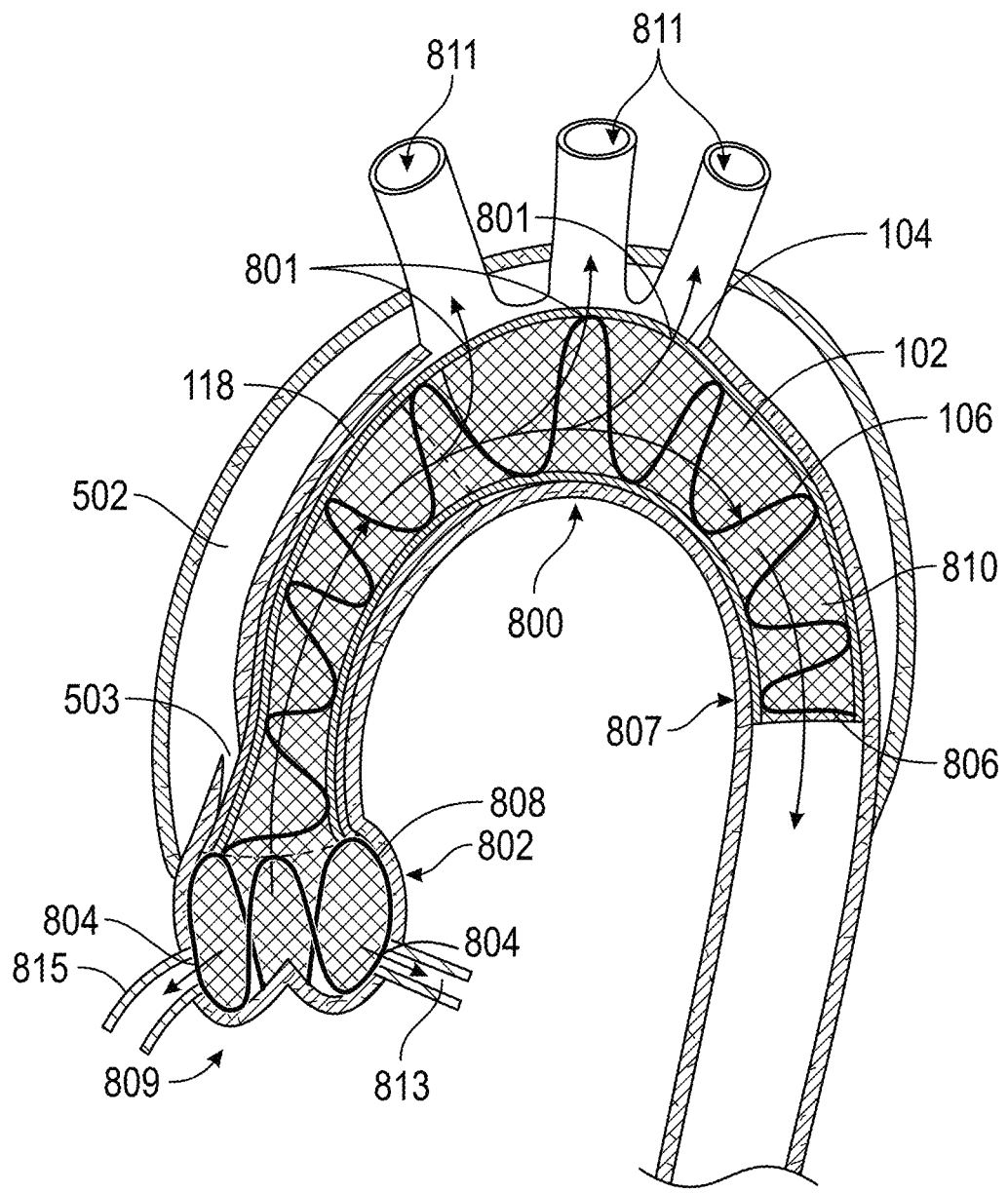
FIG. 8 is a schematic partial cross-sectional view of an aortic dissection system inside the aortic arch according to certain aspects of the present disclosure.

For example, FIG. 8 illustrates implant 102 deployed within the aortic arch 800. The implant as shown in FIG. 8 may be a sequentially deployed implant as described above, or it may be delivered as a single unit. As shown in FIG. 8, implant 102 comprises an elongate body having a proximal end 806 positioned within the descending aorta 807 and a distal end 808 positioned within the aortic root 809. The implant 102 comprises an expandable reinforcement structure, such as second implant layer 106 described above or any of the other reinforcement structures described herein, that extends from the proximal end 806 in the descending aorta 807 to or near the distal end 808 within the aortic root 809. An interface portion 802 is provided at the distal end 808 of the implant 102, which may be expandable within the aortic root 809 to anchor and secure the implant 102. The interface portion 802 may comprise an expandable wire frame and may be part of or separate from the reinforcement structure extending through the ascending aorta and descending aorta. Provided over the reinforcement structure are one more outer layers, such as implant layer 104 described above or any of the other layers described herein for covering the reinforcement structure and/or for contacting an inner wall of the aorta. For example, a porous implant layer 104 may extend from the proximal end 806 to the distal end 808 over the entire or substantially the entire reinforcement structure, optionally including the interface portion 802.

As shown in FIG. 8 (in partial cross-section for clarity), both first implant layer 104 and second implant layer 106 are curved along with the curvature of aortic arch 800, and fenestrations 801 in first implant layer 104 allow blood flow through first implant layer 104 into the carotid and subclavian arteries 811. In some embodiments, the first implant layer 104 has a porous section 810 configured to be located within the aortic arch 800 to allow blood to flow into the carotid and subclavian arteries 811. The implant 102 may further comprise, as part of the first implant layer 104 or as an additional layer, a non-porous section 118 located distal to the porous section 810 of the first implant layer 104. The non-porous section 118 can be configured to engage a wall of the aorta adjacent to the false lumen 502 and over the entry tear of dissection 503. In some embodiments, the first implant layer 104 is entirely porous. In some embodiments, the non-porous section 118 is a separate layer provided over the first implant layer 104 that is entirely non-porous.

FIG. 8 also shows how an interface portion 802 (e.g., contiguous with or coupled to first implant layer 104 and/or the second implant layer 106) can be provided at the distal end of implant 102. As shown, interface portion 802 is configured to conform to the native anatomy of the aortic valve cusps, e.g., to the sinuses of the aortic root, and includes fenestrations 804 for the left and right coronary ostia. As illustrated, the interface portion 802 may comprise an expandable wire frame having three lobes, each lobe configured to be positioned in and expandable to engage with one of the sinuses of the aortic root. Any or all of the lobes may be partially or entirely covered with a porous material or non-porous material, such as porous material of the first implant layer 104 or non-porous material of the additional implant layer 118. As illustrated, the lobes in the left coronary and right coronary aortic sinuses may extend distally beyond the left and right coronary arteries 813, 815, respectively. When covered with porous material, blood will be allowed to flow through the porous material covering these lobes into the left and right coronary arteries.

Figure 9A:
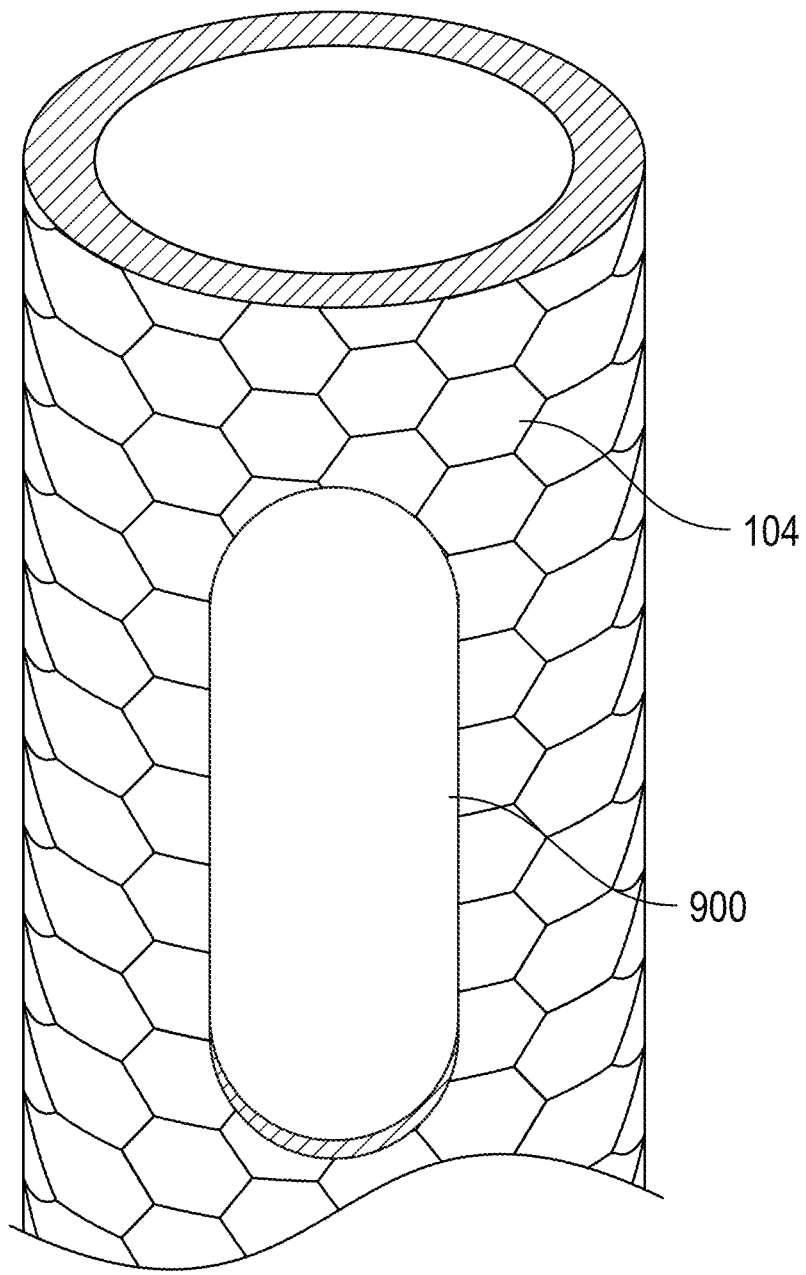
FIG. 9A is another schematic perspective, partial cross-sectional view of a graft component of an aortic dissection system according to certain aspects of the present disclosure.
Figure 9B:
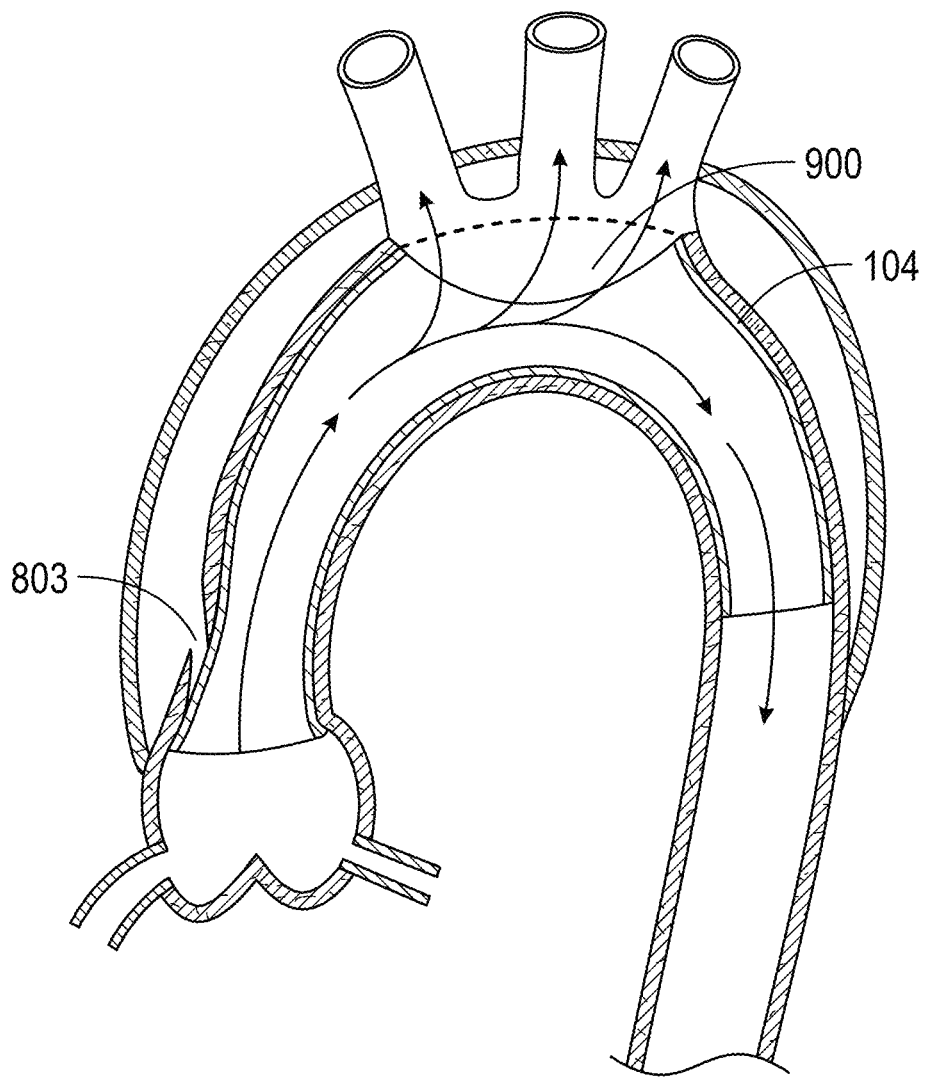
FIG. 9B is another schematic partial cross-sectional view of a graft component of an aortic dissection system inside the aortic arch according to certain aspects of the present disclosure.
Figure 9C:
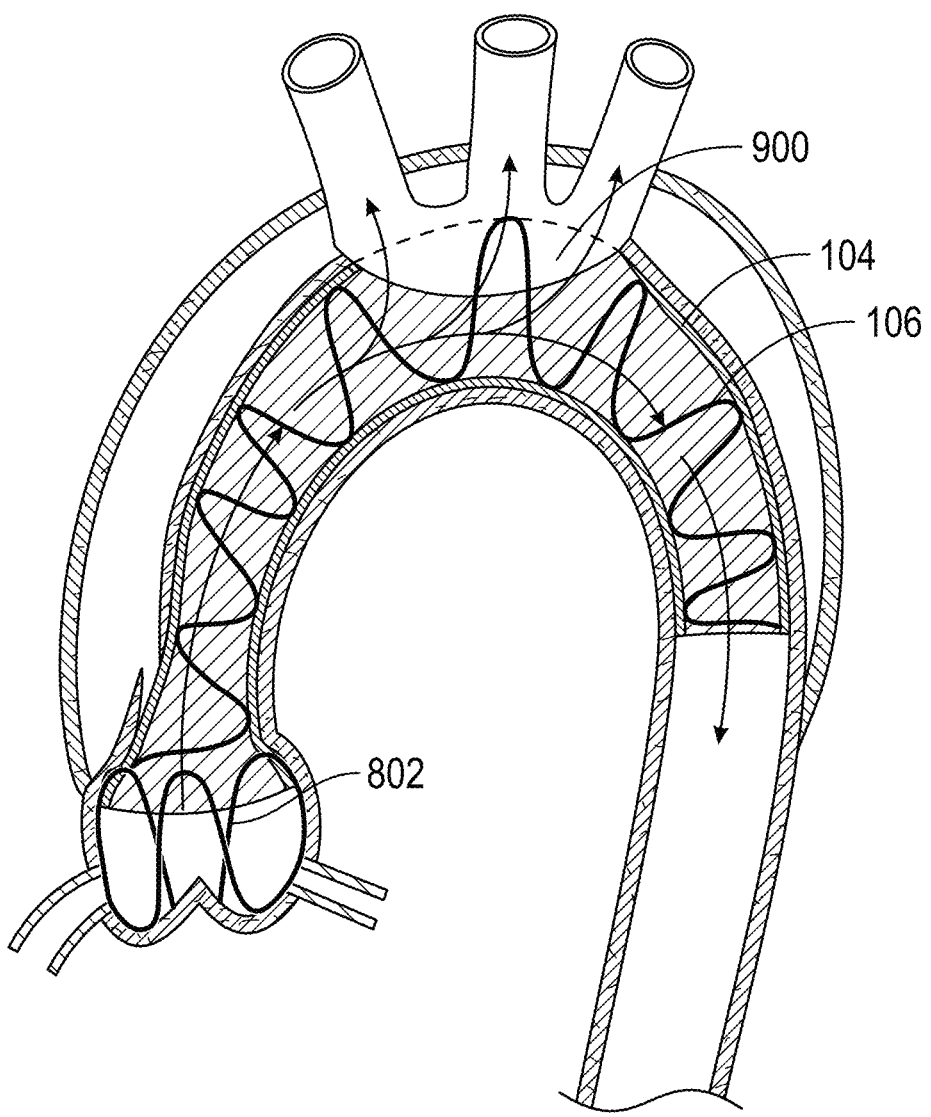
FIG. 9C is another schematic partial cross-sectional view of an aortic dissection system inside the aortic arch according to certain aspects of the present disclosure.

FIG. 9A illustrates a perspective view of another aspect of an implant 102 comprising a first implant layer 104 in a dual-layer honeycomb fabric implementation with an elongate opening 900 (e.g., for alignment with the carotid and/or subclavian arteries). FIG. 9B illustrates a partial cross-sectional view of first implant layer 104 deployed within the aortic arch. As shown in FIG. 9B, the elongate opening 900 may align with the carotid and subclavian arteries such that blood may flow through the elongate opening 900 and into the arteries. The layer 104 in this embodiment may be non-porous to prevent blood from flowing into the dissection 503. FIG. 9B illustrates the implant 102 without a reinforcement structure or second implant layer 106. FIG. 9C illustrates a partial cross-sectional view of an implant 102 comprising a first implant layer 104 like in FIG. 9A with second implant layer 106 provided within the first implant layer 104. An interface portion 802 as described above may anchor the first implant layer 104 and/or the second implant layer 106 to the aortic root.

Figure 10:
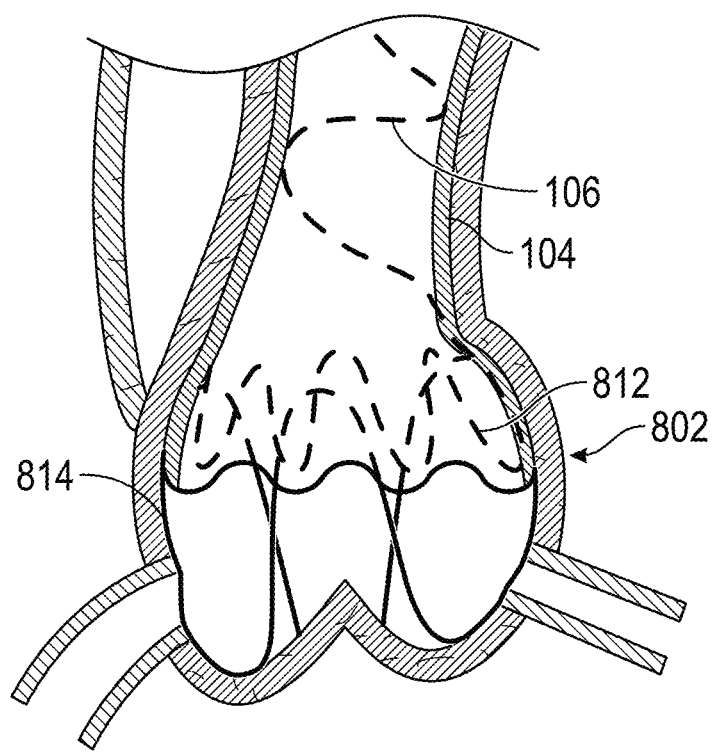
FIG. 10 is a schematic partial cross-sectional view of the distal end of an aortic dissection implant according to certain aspects of the present disclosure.

FIG. 10 illustrates an edge shape for interface portion 802 that can expand to conform to the native anatomy. The interface portion 802 may comprise a first expandable component 814. For example, the interface portion 802 can comprise a first expandable component 814 that can be configured to be positioned within the aortic root of a patient and apply radial force to one or more of the sinuses of the aortic root when expanded. The first component 814 can comprise multiple lobes, such as three lobes to form a trilobe anchoring structure, wherein the lobes are configured to engage with each of the sinuses of the aortic root and apply radial force to secure the first component 814 to the aortic root. Additionally, as shown FIG. 10, the interface portion 802 can comprise a second expandable component 812 proximal to the first expandable component 814 that can be configured to be positioned within the sinotubular junction and apply radial force to this junction when expanded. In different embodiments, the interface portion 802 can comprise either the first expandable component 814 or the second expandable component 812.

Additionally, the shape of the first implant layer 104 at the interface portion 802 may be shaped such that the first implant layer 104 does not impede blood flow through the coronary ostia. As illustrated, the first implant layer 104 may extend distally from the ascending aorta into the left and right aortic sinuses to cover only part of the interface portion 802 in the left and right aortic sinuses, but may terminate proximal to the left and right coronary arteries to allow blood to flow therethrough. The first implant layer 104 may also extend distally from the ascending aorta into the non-coronary aortic sinuses and cover part or all of the interface portion 802 in the non-coronary aortic sinuses.

Figure 11:
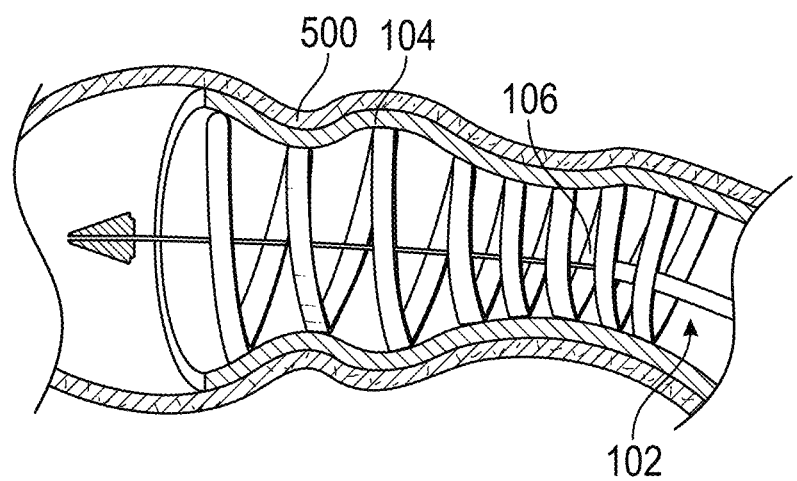
FIG. 11 is another schematic partial cross-sectional view of an aortic dissection system deployed inside the aorta according to certain aspects of the present disclosure.

FIG. 11 illustrates one example of implant 102 during deployment in a portion of blood vessel 500 with a varying diameter, showing how second implant layer 106 is variably compressible (e.g., responsive to the radial strength of the walls of blood vessel 500) to conform first implant layer 104 along the walls of the blood vessel.

Figure 12:
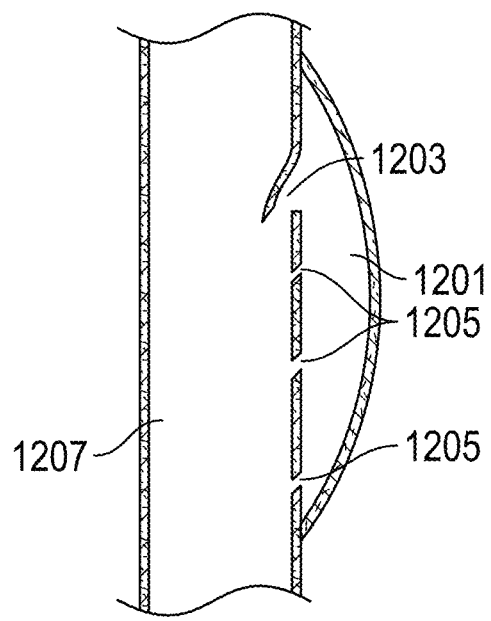
FIG. 12 is schematic cross-sectional view an aortic dissection before deployment of an aortic dissection system in accordance with certain aspects of the present disclosure.
Figure 13A:
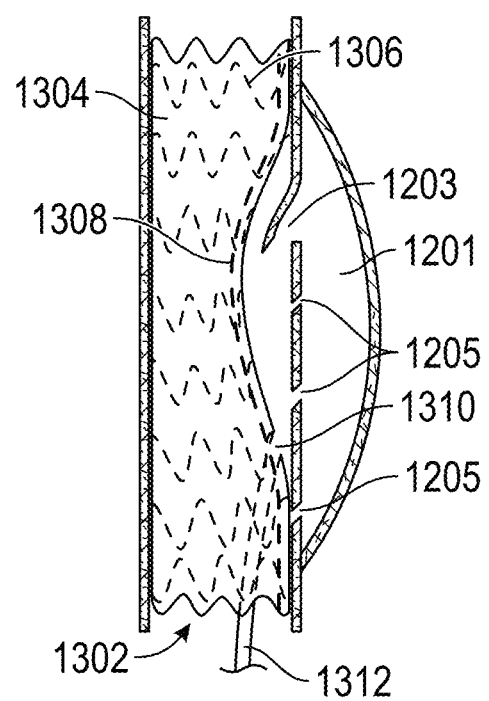
FIGS. 13A-13C are schematic partial cross-sectional views of the aorta during and after deployment of an aortic dissection implant in accordance with certain aspects of the present disclosure.
Figure 13B:
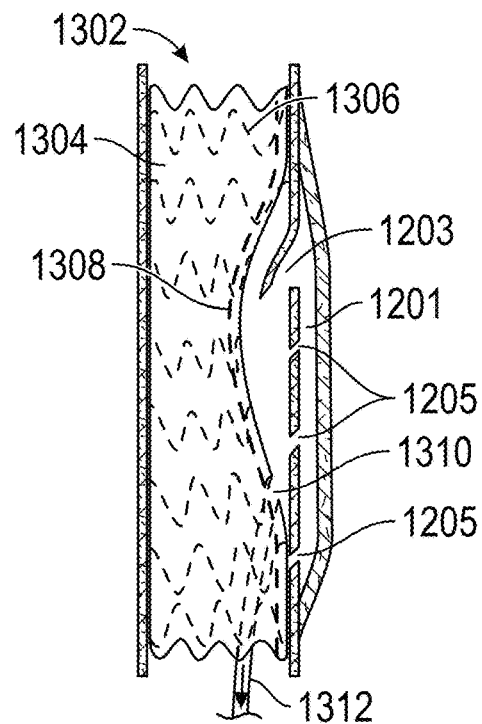
Figure 13C:
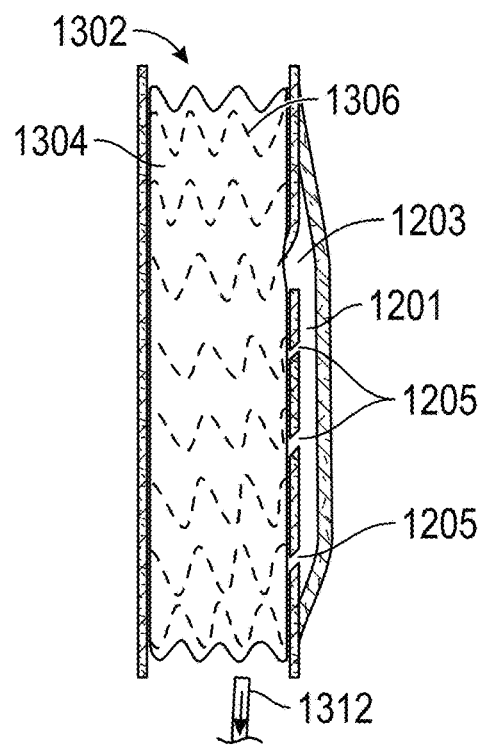

FIGS. 12-14D illustrate how, in some implementations, an implant 1302, 1402 can include features that allow further obliteration of a false lumen 1201. FIG. 12 illustrates a cross-sectional view of a blood vessel having a true lumen 1207, a false lumen 1201 associated with a dissection 1203, and natural fenestrations 1205 adjacent to the false lumen 1201. In the examples of FIGS. 13A-13C, a first implant layer 1304 is provided over a second implant layer 1306 with a suction port 1310 that provides a channel to which vacuum can be applied via a vacuum applicator 1312. The first implant layer 1304 can comprise features as described above for other first implant layers or any of the other first implant layers described herein. Moreover, the second implant layer 1306 may include features as described above for other second implant layers or any other reinforcement structures described herein. In this example, one or more longitudinal ribs 1308 can be provided to maintain a circumferential space between the outer surface of layer 1304 and the interior wall of the native aorta. The one or more longitudinal ribs 1308 may extend axially along a length of the implant 1302, and may have a stiffness greater than that of the second implant layer 1306. The one or more longitudinal ribs may have a curvature or be bowed, thereby preventing the implant layer 1306 from fully expanding. When the implant 1302 is sealed around the dissection 1203, a vacuum may be applied to channel 1310. As shown in FIG. 13B, this causes the surrounding false lumen 1201 to be reduced by drawing fluid from the false lumen 1201 through the entry tear 1203 and the natural fenestrations 1205 of the native aorta. As shown in FIG. 13C, support ribs 1308 can then be removed to allow for apposition of the implant surface to the native aorta against the media and adventitia layers, thereby minimizing the false lumen 1201 and maximizing the cross-section of the true lumen 1207.

In some embodiments, implant 1302 can include a solid, non-porous graft portion that can be used, for example, for Type B dissections that are in the descending aorta. In these examples, implant 1302 maintains a suction lumen 1310 that runs from the inner diameter of the graft to communicate with an area on the outer diameter of the graft adjacent to the false lumen 1201. Using temporary longitudinal support ribs 1308 to maintain the space (see, e.g., FIGS. 13A-13B), a vacuum is drawn in space between the implant 1302 and the false lumen 1201 to attempt to empty out the false lumen 1201 through the natural porosity 1205 of the native aorta. Once the false lumen 1201 is drawn down, then the support ribs 1308 can be removed (see, e.g., FIG. 13C) and the implanted graft 1302 can radially expand to its full diameter and further reduce the false lumen 1201 which has been emptied of pooled blood as indicated with reduced false lumen 1201 in FIG. 13C.

Figure 14A:
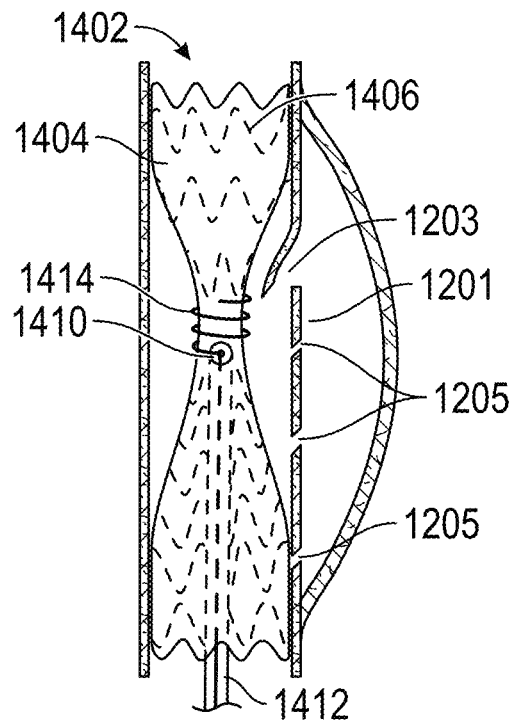
FIGS. 14A-14D are schematic partial cross-sectional views of the aorta during and after deployment of an aortic dissection implant in accordance with certain aspects of the present disclosure.
Figure 14B:
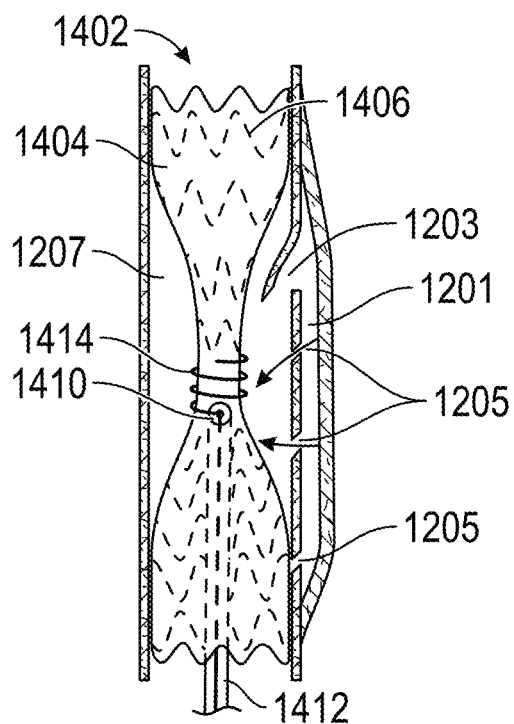
Figure 14C:
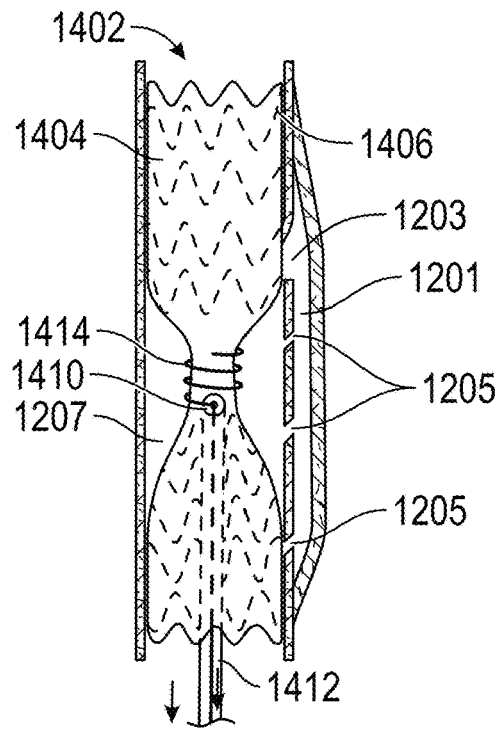
Figure 14D:
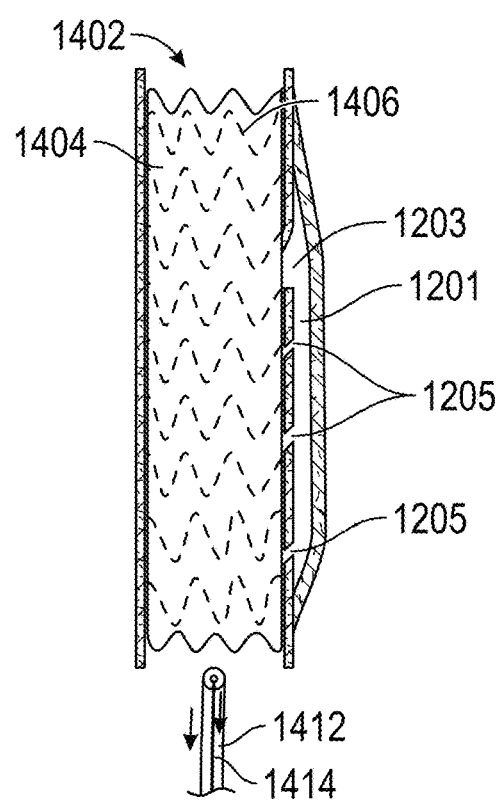

In the examples of FIGS. 14A-14D, a first implant layer 1404 is provided over a second implant layer 1406 with a suction port 1410 that provides a channel to which vacuum can be applied via a vacuum applicator 1412. In this example, an external coil 1414 can be wrapped around the outside of a central portion of the implant 1402 and passed through the suction portion 1410 and vacuum applicator 1412. The external coil 1414 is provided to maintain a circumferential space between the outer surface of first implant layer 1404 and the interior wall of the native aorta, so that when a vacuum is applied to port 1410, the surrounding false lumen 1201 would be reduced by drawing fluid from the false lumen 1201 through the entry tear 1203 and the natural fenestrations 1205 of the native aorta. As shown in FIGS. 14C-14D, the external coil 1414 can then be removed to allow for apposition of the implant surface to the native aorta against the media and adventitia layers, thereby minimizing the false lumen 1201 and maximizing the cross-section of the true lumen 1207.

In some embodiments, implant 1402 can include a solid, non-porous graft portion that can be used, for example, for Type B dissections that are in the descending aorta. In these examples, implant 1402 maintains a suction lumen 1410 that runs from the inner diameter of the graft to communicate with an area on the outer diameter of the graft adjacent to the false lumen 1201. Using the temporary external coil 1414 to maintain the space (see, e.g., FIGS. 14A-14B), a vacuum is drawn in space between the implant 1402 and the false lumen 1201 to attempt to empty out the false lumen 1201 through the natural porosity 1205 of the native aorta. Once the false lumen 1201 is drawn down, then the external coil 1414 can be removed (see, e.g., FIGS. 14C-14D) and the implanted graft 1402 can radially expand to its full diameter and further reduce the false lumen 1201 which has been emptied of pooled blood as indicated with reduced false lumen 1201 in FIG. 14D.

FIGS. 12-14D illustrate, simply for convenience, deployment of implant 1302, 1402 in a substantially straight portion of blood vessel. However, it should be appreciated that first implant layer 1304, 1404 and second implant layer 1306, 1406 as described allow implant 102 to be deployed in curved portions of a blood vessel, and/or in portions of a blood vessel having a varying size.

Figure 1B:
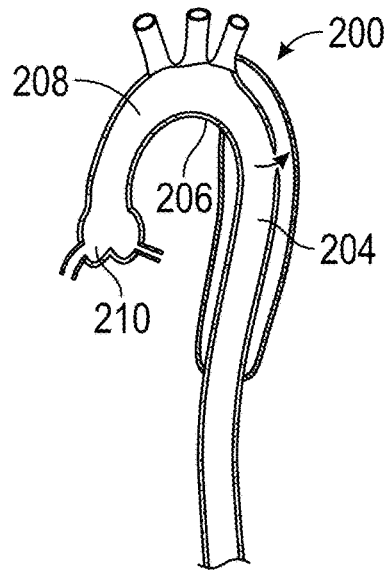
Figure 1C:
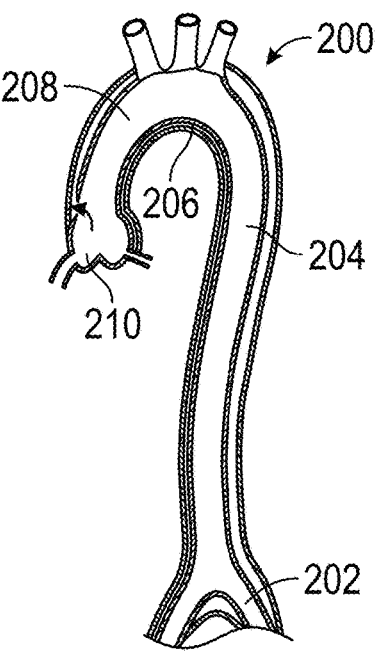
FIGS. 1C-1F show the common classifications of Aortic Dissections DeBakey Type I, II and III.
Figure 1D:
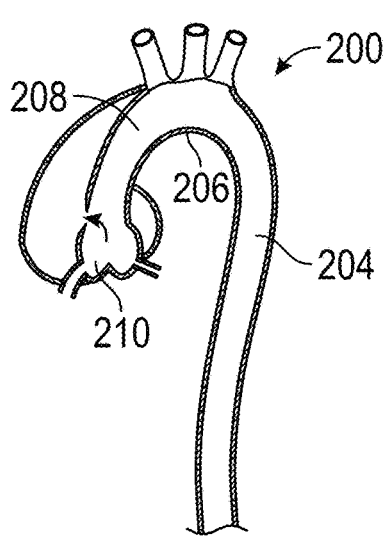
Figure 1E:
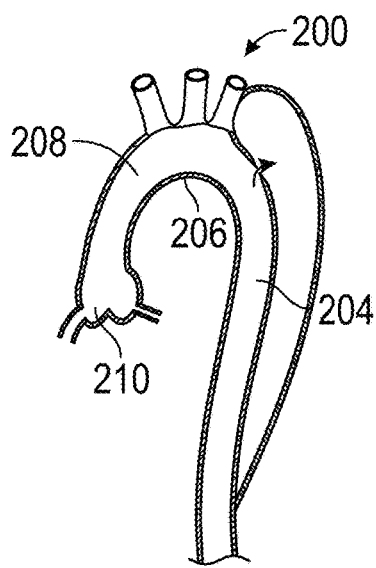
Figure 1F:
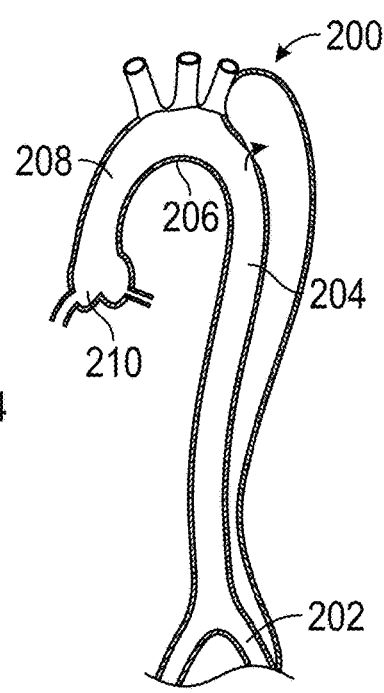

Generally, porous versions of implant 102 may be useful for any Type A (I or II) dissections (see, e.g., FIG. 1A) that require extending through the head vessels, and can also be applied to some Type B incidents (see, e.g., FIG. 1B). The non-porous graft option 1302, 1402 of FIGS. 13A-14D may be more applicable to certain Type B configurations. Variable porosity of layer 104, 1304, 1404 (e.g., one section solid, another segment porous, or different degrees of porosity) can be used to offer solutions for different dissection or aneurysm configurations.

Figure 15A:
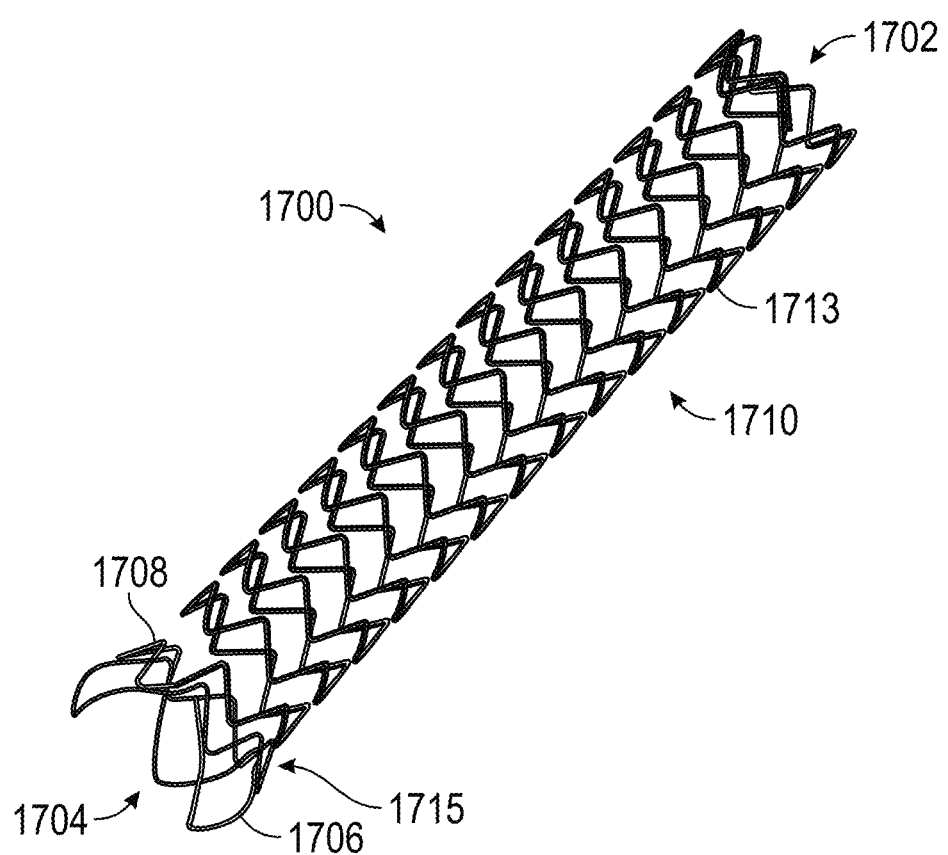
FIG. 15A is perspective view of an embodiment of an expandable support structure of an aortic dissection implant according to certain aspects of the present disclosure.
Figure 15B:
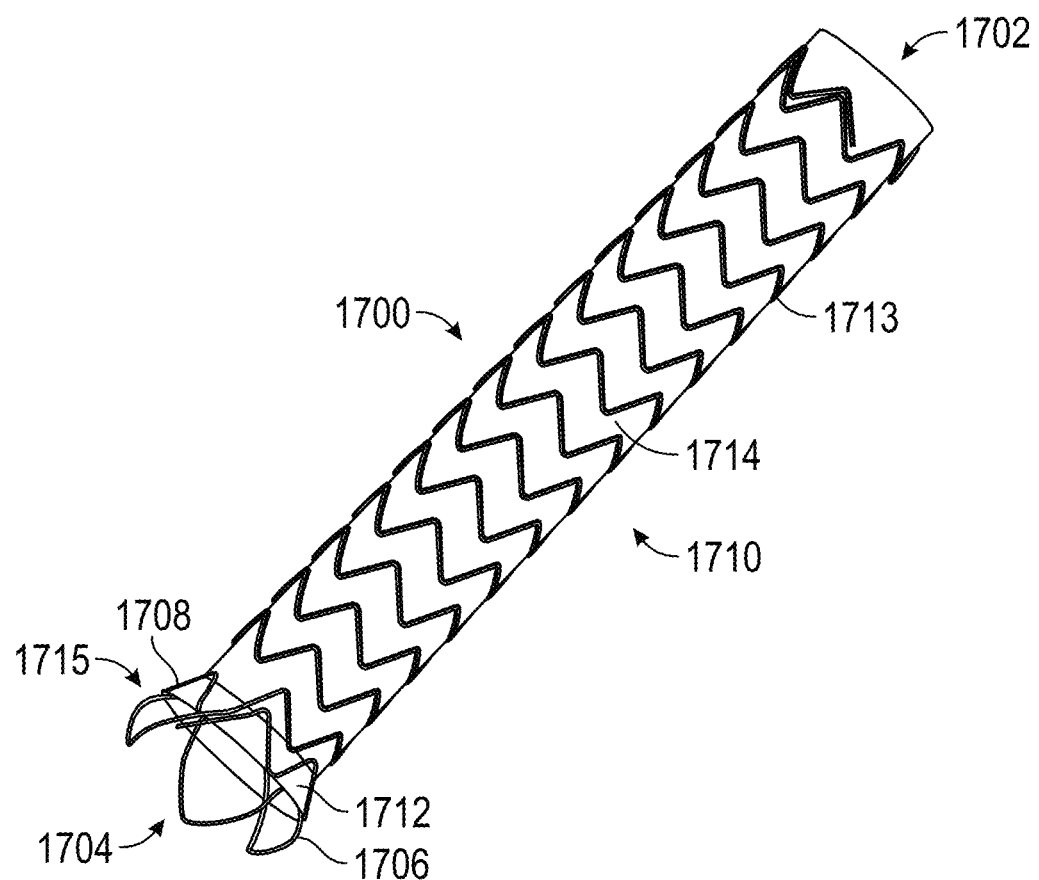
FIG. 15B is a perspective view of an embodiment of the expandable support structure depicted in FIG. 15A with a layer provided within the structure according to certain aspects of the present disclosure.
Figure 15C:
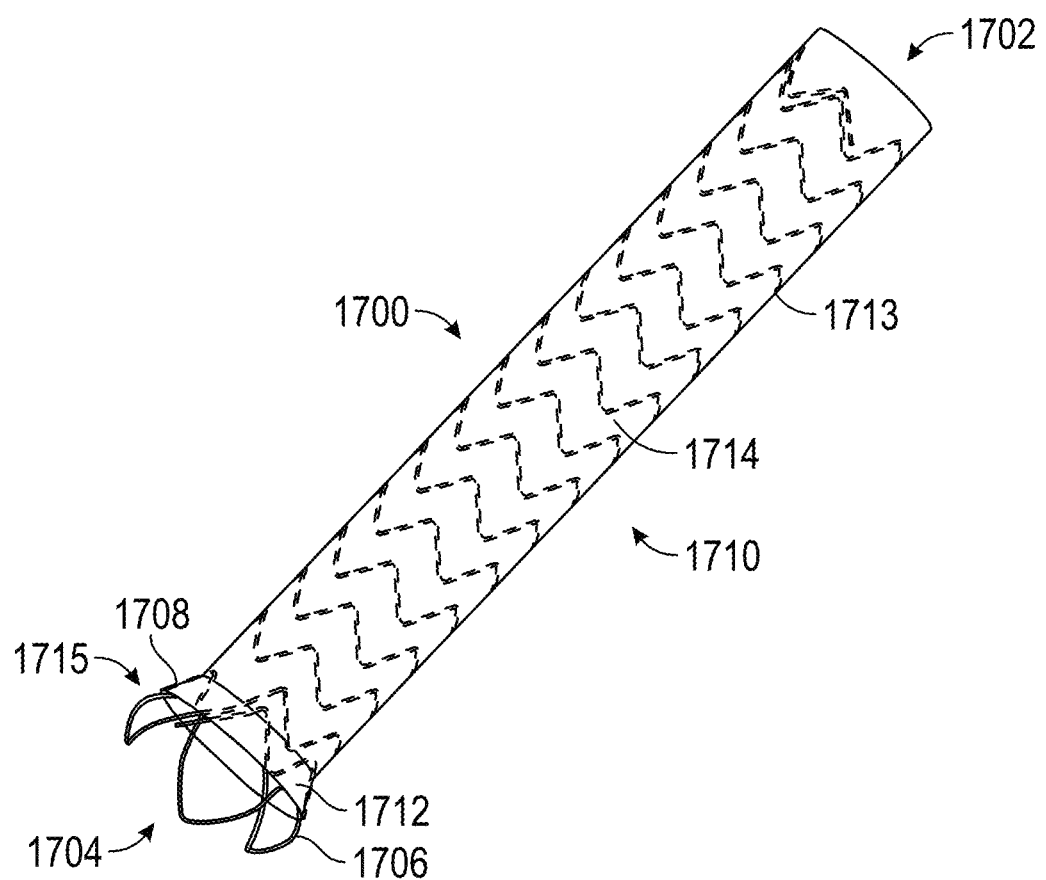
FIG. 15C is a perspective view of an embodiment of the expandable support structure depicted in FIG. 15A with a layer provided over the structure according to certain aspects of the present disclosure.

FIGS. 15A-15C depict another embodiment of an aortic dissection implant 1700. FIG. 15A depicts an implant layer such as described above that comprises a generally tubular, expandable support structure that extends from a proximal end 1702 to a distal end 1704. The embodiment of the expandable support structure depicted in FIG. 15A shows a wire frame or wire coil 1713 with a zig-zag or Z-shaped pattern along a cylindrical portion 1710 of the coil 1713. Additionally, the expandable support structure can comprise other patterns that are suited for being used to treat an aortic dissection. Furthermore, the expandable support structure may be a laser cut structure, a braid or may be formed in another open configuration that can accommodate the curvature of the native aorta. The expandable support structure may also be completely or partially radiopaque and/or echogenic to enhance visualization intra-procedurally. The cylindrical portion 1710 of the coil 1713 can be configured to extend from the descending aorta to the ascending aorta and curve along with a curvature of the aortic arch when expanded within the aorta.

At the distal end 1704, the implant 1700 may comprise an expandable anchoring structure 1715 such as the interface portion described above. The expandable anchoring structure 1715 may have an enlarged cross-sectional diameter when expanded as compared to the cylindrical portion 1710. The expandable anchoring structure 1715 can comprise one or more components. For example, the expandable anchoring structure 1715 can comprise a first expandable component 1706, such as the first expandable component described above, that can be configured to be positioned within the aortic root of a patient and apply radial force to the sinuses of the aortic root when expanded. The first component 1706 can comprise multiple lobes, such as three lobes to form a trilobe anchoring structure, wherein the lobes are configured to engage with each of the sinuses of the aortic root and apply radial force to secure the first component 1706 to the aortic root. Additionally, as shown FIG. 15A, the expandable anchoring structure 1715 can comprise a second expandable component 1708 proximal to the first expandable component 1706, such as the second expandable component described above, that can be configured to be positioned within the sinotubular junction and apply radial force to this junction when expanded. The second expandable component 1718 may have a frustoconical shape in some embodiments, with a smaller diameter proximal end and a larger diameter distal end, to provide a transition between the cylindrical portion 1710 and the enlarged expandable component 1706. In different embodiments, the expandable anchoring structure 1715 can comprise either the first expandable component 1706 or the second expandable component 1708.

In some aspects, the wire frame 1713 may be a continuous wire that forms the first expandable component 1706, the second expandable component 1708 and the cylindrical portion 1710. In other aspects, the first expandable component 1706, the second expandable component 1708 and the cylindrical portion 1710 may be formed from separate wire frames. The wire frame 1713 may be formed from one or more of a metal (e.g., stainless steel, nitinol, or the like), a polymer, a biological material, a bio-absorbable material, and/or other suitable materials. In some aspects, the wire frame 1713 may have an overall length of between approximately 12-15 cm, a cross-sectional width or diameter of the wire of approximately 0.5 mm, and a resting diameter in the cylindrical portion 1710 of approximately 40 mm to approximately 45 mm. The wire frame 1713 may be radially compressible to a diameter of approximately 10 mm or less. The expandable anchoring structure 1715 may have a diameter of approximately 45 to 55 when expanded.

FIGS. 15B-15C illustrate embodiments of the aortic dissection implant that comprises the wire frame 1713 with a layer 1714 provided either within (FIG. 15B) or over (FIG. 15C) the wire frame 1713. The layer 1714 can extend from the proximal end 1702 of the wire frame 1713 to the distal end 1704 of the wire frame 1713. In some embodiments, the layer 1714 may cover the second expandable component 1708 of the expandable anchoring structure 1715 and part of the first expandable component 1706 of the expandable anchoring structure 1715. This configuration allows for the coronary ostia to remain uncovered after implantation of the aortic dissection implant, which allows blood to flow freely through the ostia. In other embodiments, the layer 1714 may extend to the distal end of the expandable anchoring structure 1715.

In some aspects, the layer 1714 can be formed from fabric, metal, polymer or a biological tissue. The layer 1714 is sized such that it is capable of reaching a diameter just slightly beyond that of the native aorta (e.g., a maximum diameter of about 40 mm to about 45 mm) when fully expanded with the wire frame 1713 inside. In other implementations, the layer 1714 can have a resting diameter of 35 mm and an expanded diameter of 40 mm. The material of the layer 1714 may be flexible enough to accommodate the curvature of the aortic arch. In some implementations, the entire length of layer 1714 could be porous. In other implementations, the entire length of layer 1714 may be non-porous. In still other implementations, the level of porosity may vary throughout the length of layer 1714. For example, the portion of the layer 1714 along a distal portion of the cylindrical portion 1710 may be non-porous and the portion of the layer 1714 along a proximal portion of the cylindrical portion 1710 may be porous (e.g., as shown in FIG. 8). In this embodiment, the porous section of the layer 1714 can be configured to curve along the curvature of the aortic arch and allow blood to flow into the carotid and subclavian arteries of the patient. The non-porous section of this embodiment can be configured to engage with the wall of the aorta adjacent a false lumen associated with the dissection. The wire frame 1713 provides hoop strength and radial force beyond that of the layer 1714, and serves to enhance the apposition of the layer 1714 against the intima.

Figure 15D:
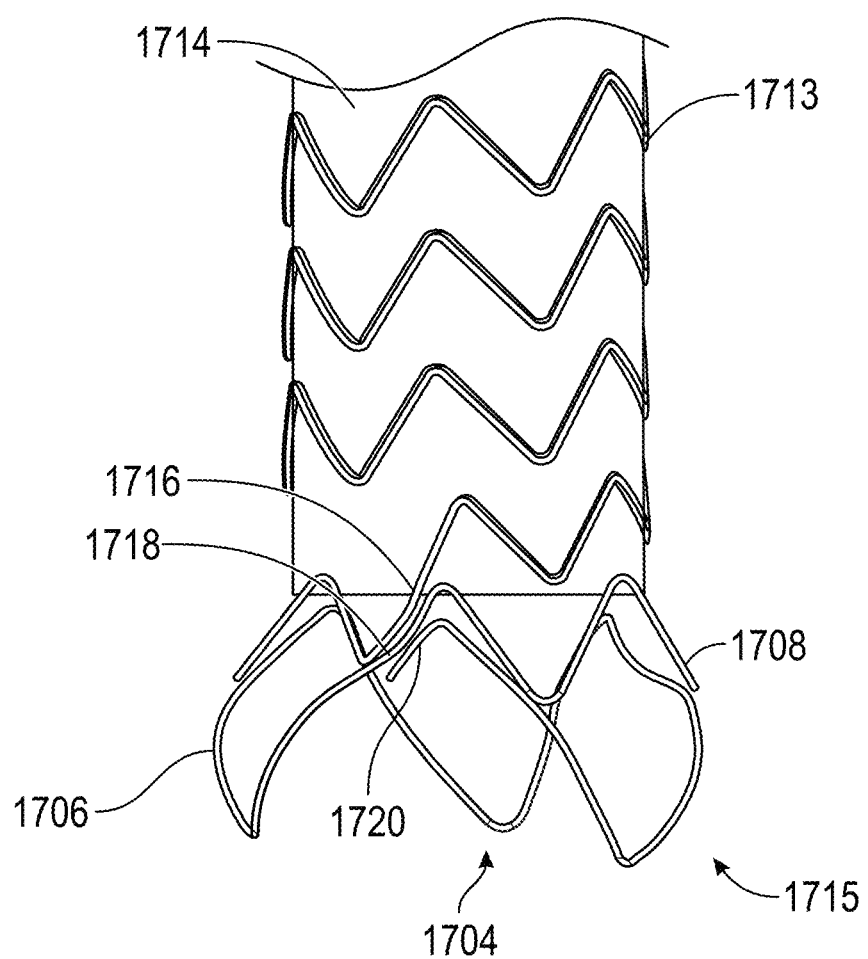
FIG. 15D is a perspective view of the distal end an aortic dissection implant according to certain aspects of the present disclosure.

In some embodiments, the wire frame 1713 shown in FIGS. 15A-15D can be created from a single piece of wire. FIG. 15D depicts the distal end 1704 of the embodiment of the aortic dissection implant shown in FIGS. 15A-15B. The back portion of the second expandable component 1708 and the frustoconical portion of the layer 1714 covering the second expandable component are not shown in FIG. 15D for clarity. A distal portion 1720 of the single wire can be located at the distal end 1704 of the wire frame 1713. The single wire can be bent to form the trilobe structure of the first component 1706 of the expandable anchoring mechanism. At a first transition portion 1718 of the single wire, the wire can be bent in such a way to form the second component 1708 of the expandable anchoring structure. As illustrated, the second component 1708 may be made with the wire 1713 forming a sine wave around a circumference of the implant. At a second transition portion 1716 of the single wire, the wire can be bent to begin forming the Z-shaped or zig-zag pattern of the cylindrical portion 1710 of the wire frame 1713 following generally spiral or helical shaped path. After the wire frame 1713 is formed, the distal portion 1720 is crimped or welded to the first transition portion 1718. Additionally, at the proximal end 1702 of the coil 1700, as shown in FIG. 15B, a proximal end of the single wire can be crimped or welded to the portion of the coil 1700 directly distal to the proximal end of the single wire. In other embodiments, the coil 1700 can comprise multiple wires welded together. In other embodiments, a single wire may extend from the distal (or proximal end) of the implant, to the other end, and back.

Figure 16:
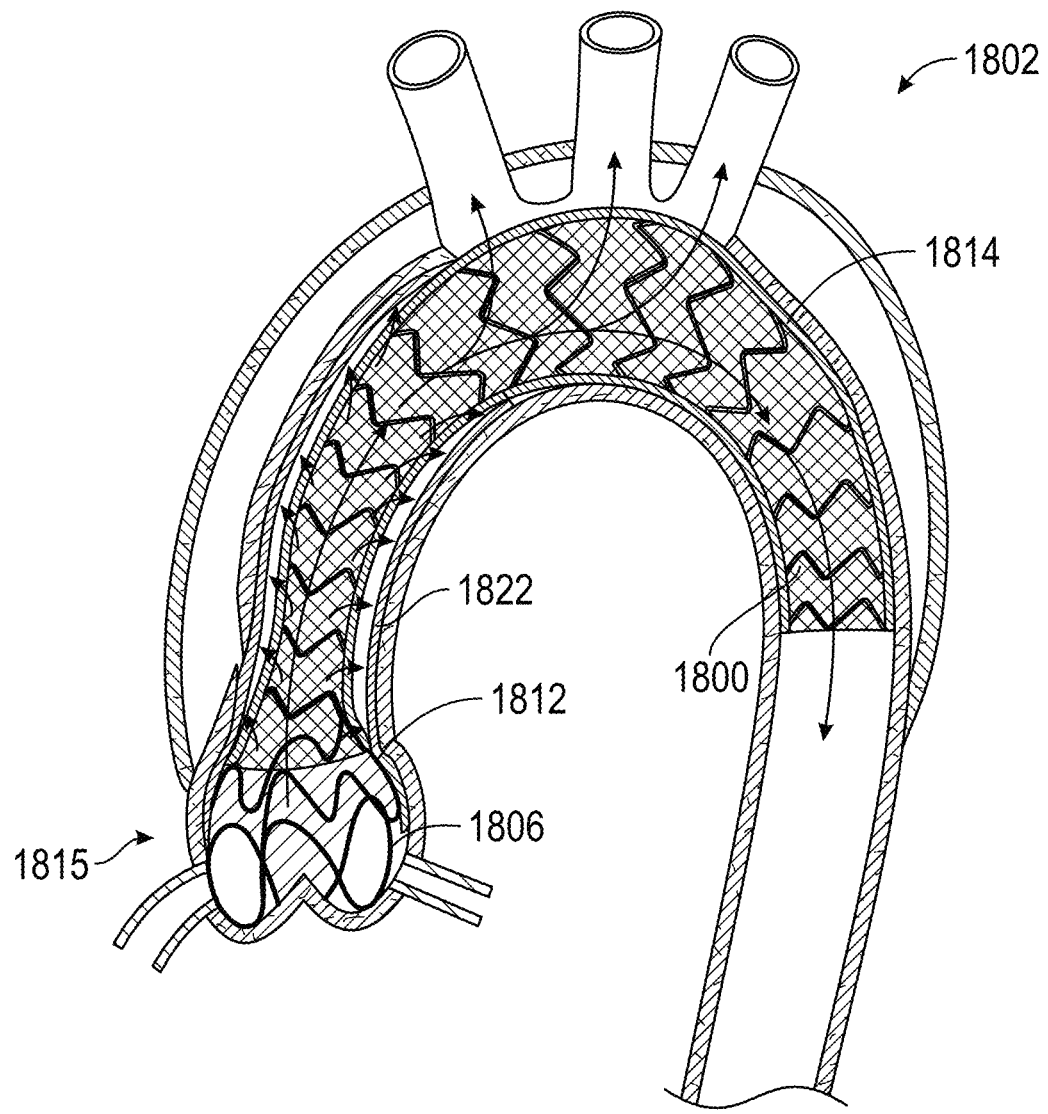
FIG. 16 is a schematic partial cross-sectional view of an aortic dissection implant in the aortic arch according to certain aspects of the present disclosure.

FIG. 16 illustrates a partial cross-sectional view of another embodiment of an implant 1802 deployed within the aortic arch and extending between the descending aorta, through the ascending aorta, and into the aortic root. In this embodiment, the implant 1802 may comprise a first layer 1814, a second layer 1822, and an expandable support structure 1800. The expandable support structure 1800 may be similar to the wire frame 1713 depicted in FIGS. 15A-15D and described in the foregoing paragraphs, or it may be similar to any of the earlier described embodiments of reinforcement structures. The expandable support structure 1800 may comprise a cylindrical coil or wire frame that can comprise a sinusoidal wave pattern, Z-shape or zig-zag pattern. The expandable support structure 1800 can be configured to extend from the descending aorta to the ascending aorta and curve along with the curvature of the aortic arch when expanded within the aorta. In some aspects, the distal end of the expandable support structure may comprise an expandable anchoring structure 1815 as described above. In some embodiments, the expandable anchoring structure 1815 can comprise an expandable trilobe structure 1806 that can be configured to be positioned within the aortic root of a patient and apply radial force to the sinuses of the aortic root. In some embodiments, the expandable anchoring structure 1815 may comprise a sinusoidal wave structure 1812 that may be configured to be positioned within the sinotubular junction and apply radial force to the sinotubular junction. In the embodiment shown in FIG. 16, the expandable anchoring structure 1815 comprises both the expandable trilobe structure 1806 and the sinusoidal wave structure 1812.

In some aspects, the implant 1802, and particularly the expandable support structure 1800, may be configured to expand within at least the descending aorta to press against and apply radial force to the inner wall of the descending aorta. In such embodiments, a diameter of the expandable support structure in at least a proximal portion thereof is larger than an inner diameter of the descending aorta. The implant 1802 may also be configured such that a distal portion of the implant, and particularly a distal portion of the expandable structure, is smaller than an inner diameter of the ascending aorta.

The first layer 1814 may be provided over the expandable support structure 1800 and may be configured to extend from the proximal end of the expandable support structure 1800 at least to the sinusoidal wave structure 1812. In some aspects, the first layer 1814 can be formed from fabric, metal, polymer or a biological tissue, and may be made of any of the materials described above for layer 104. The first layer 1814 may be sized such that it is capable of reaching a diameter just slightly below that of the native ascending aorta (e.g., a maximum diameter of about 35 mm) when fully expanded with the expandable support structure 1800 inside. In other implementations, the first layer 1814 can have resting diameter of 35 mm and an expanded diameter of 40 mm such that it could be expanded by the support structure 1800 to contact the inner most wall of the native descending aorta. The material of the first layer 1814 may be flexible enough to accommodate the curvature of the aortic arch. In some implementations, the entire length of first layer 1814 may be non-porous or the level of porosity may vary throughout the length of first layer 1814. In the embodiment of the aortic dissection implant shown in FIG. 16, the entire length of first layer 1814 is porous. The porosity of the first layer 1814 could be configured to allow blood to flow into the carotid and subclavian arteries of the patient. The expandable support structure 1800 provides hoop strength and radial force beyond that of the layer 1814, and serves to enhance the apposition of the layer 1814 against the intima.

The second layer 1822 may be provided over the first layer 1814 and may be configured to contact the site of the aortic dissection and the aortic wall adjacent to the false lumen. In some aspects, the length of the second layer 1822 may be less than the length of the first layer 1814. The second layer can extend along one of the lobes of the trilobe structure 1806, e.g., the lobe positioned in the non-coronary aortic sinus, and the other two lobes remain uncovered so that blood may flow through the coronary ostia. The second layer 1822 can be formed from fabric, metal, polymer or a biological tissue, including any of the materials that may be utilized for the first layer 1814. In the embodiment of the second layer 1822 shown in FIG. 16, the entire length of the second layer 1822 is non-porous.

In some embodiments, both ends of the second layer 1822 may be sealed to the first layer 1814 and the second layer 1822 may be configured to expand like a balloon when blood flows through the implant, as indicated by the arrows in FIG. 16. In particular, blood may flow through the first layer 1814 and expand the second layer 1822 such that there is space between the first layer 1814 and the second layer 1822. The expanded diameter of the second layer 1822 may be larger than the diameter of the first layer 1814 (e.g., 45 mm for 1822 versus 35 mm for 1814). The second layer 1822 may remain inflated against the aortic wall such that the second layer 1822 applies radial force to the aortic dissection site to seal the entry tear prevent blood from flowing into the false lumen. In some instances, an additional (third) layer that is non-porous may be disposed between the first porous layer 1814 and the second non-porous layer 1822 such that the third layer provides for a one-way valve that allows blood to enter the space between layers 1814 and 1822 but prevents it from exiting. This could be accomplished by laser cutting or otherwise creating gills, slots or flaps in the third layer that can open into the space during systole when blood pressure is highest but close against the first porous layer when that pressure is reduced during diastole preventing the blood from exiting.

In another embodiment, the aortic dissection implant can comprise a single layer that extends from the distal end to the proximal end of the expandable support structure. The single layer can comprise an inflatable non-porous section and a porous section proximal to the inflatable non-porous section. The inflatable non-porous section may be similar to the second layer 1822 and the porous section may be similar to the first layer 1814 shown in FIG. 16 and described in the foregoing paragraphs.

Figure 17:
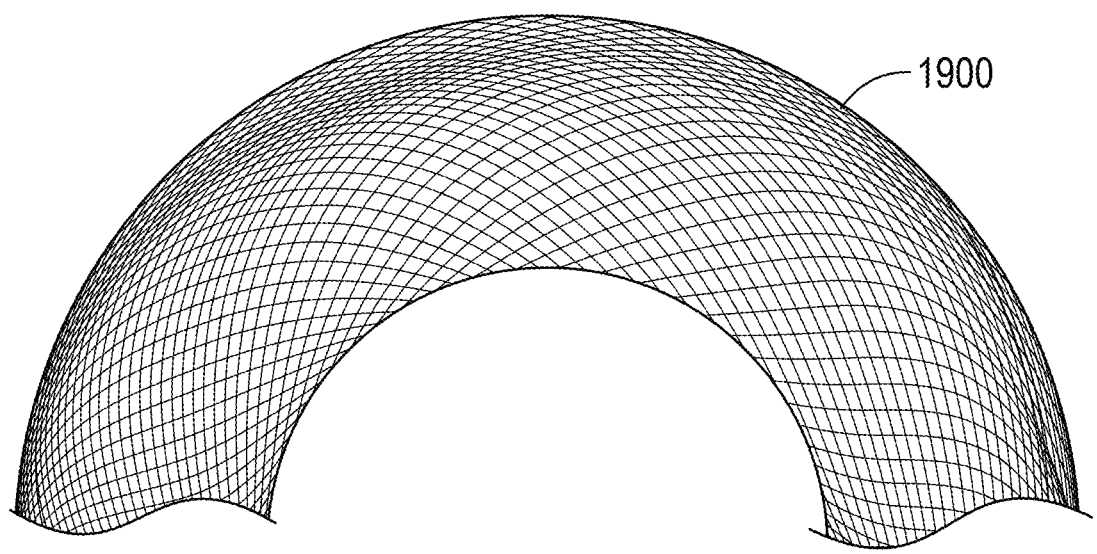
FIG. 17 is a schematic perspective view of another embodiment of an expandable support structure of an aortic dissection implant according to certain aspects of the present disclosure.

FIG. 17 illustrates another embodiment of an expandable support structure 1900. The expandable support structure 1900 can comprise a braided configuration, as illustrated in FIG. 19, and be configured to extend from the descending aorta to the ascending aorta and curve along with the curvature of the aortic arch when expanded within the aorta. In some aspects, the expandable support structure 1900 may be formed from one or more of a metal (e.g., stainless steel, nitinol, or the like), a polymer, a biological material, a bio-absorbable material, and/or other suitable materials. In other aspects, the expandable support structure 1900 may have length of approximately 15 cm and a diameter of approximately 40 mm. This embodiment of an expandable support structure 1900 may be used in the different embodiments described in the foregoing paragraphs.

Figure 18:
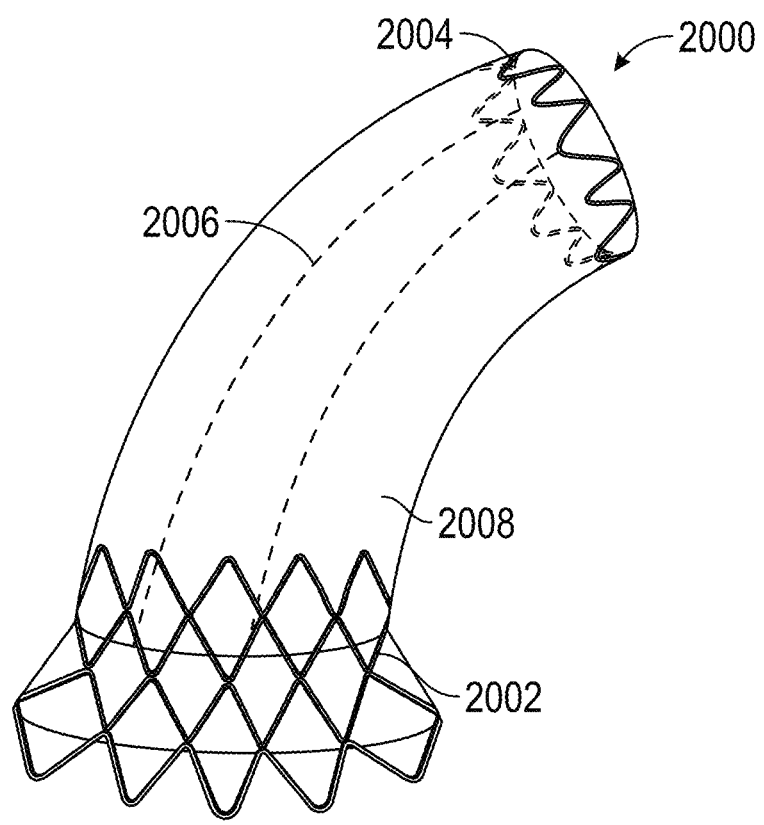
FIG. 18 is a schematic perspective view of an embodiment of an expandable support structure of an aortic dissection implant according to certain aspects of the present disclosure.

FIG. 18 depicts another embodiment of a first implant layer 2000. The first implant layer 2000 can comprise a layer 2008, a distal expandable support structure 2002, a proximal expandable support structure 2004, and an axial support structure 2006. In some aspects, the layer 2008 may be non-porous and can be formed from fabric, metal, polymer or a biological tissue. The layer 2008 can be cylindrical in shape and be configured to be flexible such that the layer 2008 can conform to the shape of the ascending aorta. In some embodiments, length of the layer 2008 may be adjusted at the time of the procedure prior to inserting the first implant layer 2000 into the patient. In some aspects, the layer 2008 can have a length of approximately 4 cm to 8 cm and a diameter of approximately 30 mm to 40 mm. The distal portion of the layer 2008 may form a frustoconical shape in some embodiments, with a smaller diameter of approximately 30 mm at a proximal end and a larger diameter of approximately 40 mm at a distal end.

The distal and proximal expandable support structures 2002, 2004 may be provided over or within the layer 2008 and apply radial force to layer 2008 against the intima of the ascending aorta when expanded within the ascending aorta. The distal expandable support structure 2002 may comprise a zig-zag pattern. The proximal expandable structure 2004 may comprise a sine wave pattern, a sine wave pattern and/or a trilobe pattern. In some aspects, the distal and proximal expandable support structures 2002, 2004 may be formed from one or more of a metal (e.g., stainless steel, nitinol, or the like), a polymer, a biological material, a bio-absorbable material, and/or other suitable materials. The diameter of the distal expandable support structure 2002 may be between 35 mm and 40 mm. The diameter of the proximal expandable support structure 2004 may be approximately 30 mm.

The first implant layer 2000 may also comprise an axial support structure 2006. The axial support structure 2006 may be provided over, within, or interwoven into the layer 2008. The axial support structure 2006 may extend between a distal end and a proximal end of the layer 2008 and may provide reinforcement to the first implant layer 2000.

The first implant layer can be deployed within a patient's aorta to provide force against the site of an aortic dissection. Following the placement of first implant layer 2000, a second long-term support structure (e.g., the expandable support structure depicted in FIG. 15A or 17) may be deployed inside of the first implant layer along the aortic arch and across the carotid and subclavian arteries to the descending aorta. Prior to deployment, the length and/or diameter of the first expandable support structure of FIG. 18 can be sized separately from the later deployed expandable support structure.

Figure 19A:
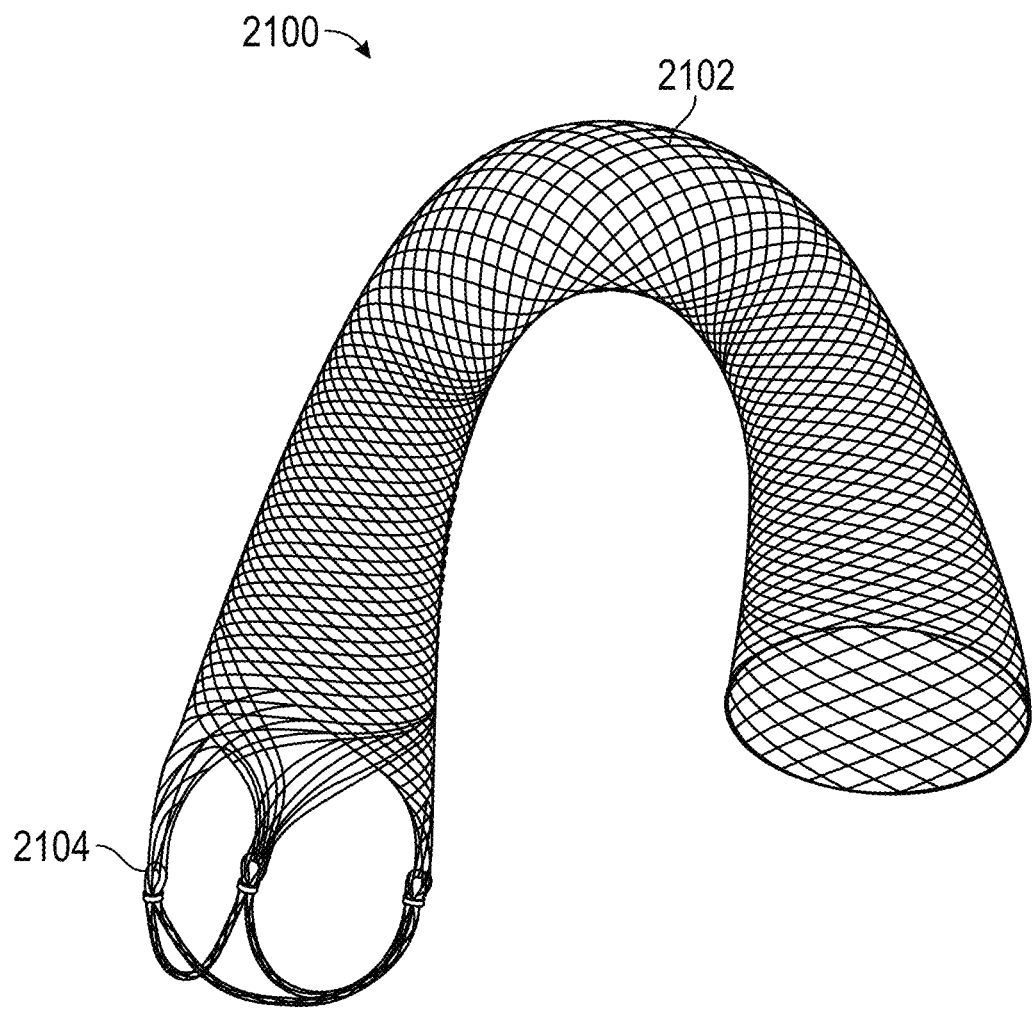
FIGS. 19A-19B are perspective views of an embodiment of an expandable support structure of an aortic dissection implant according to certain aspects of the present disclosure.
Figure 19B:
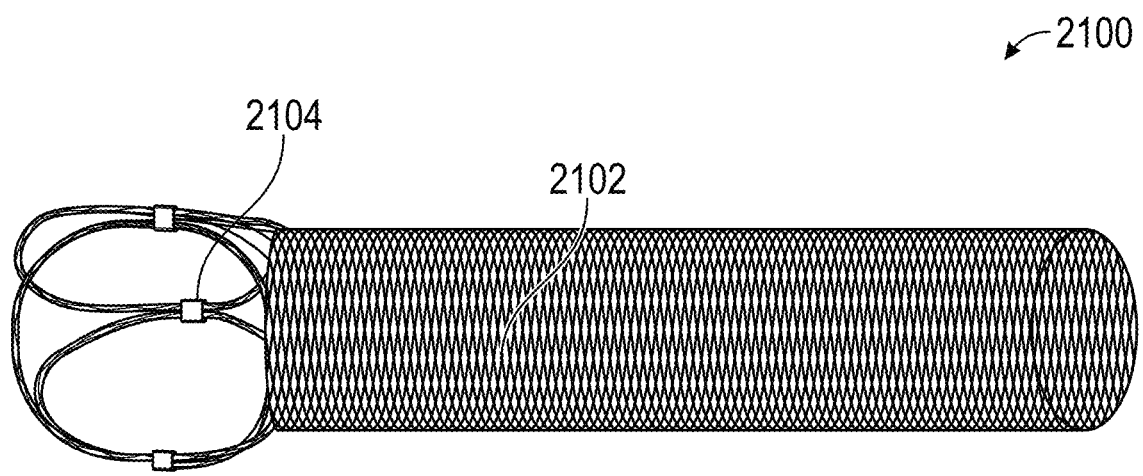

FIGS. 19A and 19B illustrate another embodiment of the expandable support structure. This embodiment of the expandable support structure 2100 may have a braided configuration, similar to the embodiment described in FIG. 17, and be configured to extend from the descending aorta to the ascending aorta and curve along with the curvature of the aortic arch when expanded within the aorta. In some aspects, the expandable support structure 2100 may be formed from one or more of a metal (e.g., stainless steel, nitinol, or the like), a polymer, a biological material, a bio-absorbable material, and/or other suitable materials. In other aspects, the expandable support structure 2100 may have length of approximately 15 cm and a diameter of approximately 40 mm. This embodiment of an expandable support structure 2100 may be used in the different embodiments described in the foregoing paragraphs.

FIG. 19A depicts the expandable support structure 2100 in a curved orientation and FIG. 19B depicts the expandable structure 2100 in a straight orientation. The expandable support structure 2100 may comprise an anchoring mechanism 2104 at the distal end and a cylindrical portion 2102 proximal to the anchoring mechanism 2104. The anchoring mechanism 2104 may comprise three lobes that can be configured to be positioned within the aortic root of a patient and apply radial force to the sinuses of the aortic root. The cylindrical portion 2102 may be configured to extend from the descending aorta to the ascending aorta and curve along with the curvature of the aortic arch when expanded within the aorta.

In some embodiments, the aortic dissection implant, as described in the foregoing paragraphs, can be preformed during manufacturing. For example, the implant can be preformed to include a bend with a radius of curvature of approximately 35 mm and an angle of curvature of 150 degrees to 180 degrees. This bend can be configured to be positioned along the curvature of the aortic arch. In some embodiments that include trilobe anchoring structures, the preformed shape may be aligned with respect to the non-coronary aortic sinus (e.g. the major bend of the aortic arch could be approximately 90 degrees from the non-coronary aortic sinus). In other embodiments, specific features like the window 900 in FIG. 9A-C could also be aligned with the pre-formed curvature of the implant and/or specific trilobe features as noted above.

In some embodiments, the aortic dissection implant, as described in the foregoing paragraphs, may have variable dimensions to assist in securing and anchoring of the implant. For example, the implant in an expanded configuration may have a relatively larger diameter at its distal end (e.g., about 35 mm or more, to anchor for example in the aortic root and/or the sinotubular junction), a relatively smaller diameter in an middle portion (e.g., about 30 mm or less, to position for example in the ascending aorta without exerting additional radial force on the fragile aortic wall where a dissection has occurred), and a relatively larger diameter at its proximal end (e.g., about 35 mm or more, to anchor for example in the descending aorta). In other embodiments it may have a relatively smaller diameter in its proximal region (e.g., 30 mm or less) to conform to a smaller descending aorta diameter and a relatively larger diameter in the middle portion if the ascending aorta diameter is much larger and dilated (e.g., 40 mm).

It is understood that any specific order or hierarchy of blocks in the processes disclosed is an illustration of example approaches. Based upon implementation preferences, it is understood that the specific order or hierarchy of blocks in the processes may be rearranged, or that not all illustrated blocks be performed. Any of the blocks may be performed simultaneously. In one or more embodiments, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

The subject technology is illustrated, for example, according to various aspects described above. The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that some or all steps, operations, or processes may be performed automatically, without the intervention of a user. Method claims may be provided to present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the appended claims. Moreover, nothing disclosed herein is intended to be dedicated to the public regardless of whether such disclosure is explicitly recited in the claims. No claims element is to be construed under the provisions of 35 U.S.C. § 112 (f) unless the element is expressly recited using the phrase "means for" or, in the case of a method, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Brief Description of the Drawings, and Claims of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in any claim. Rather, as the following claims s reflect, inventive subject matter lies in less than all features of a single disclosed configuration or operation. The following claims are hereby incorporated into the Detailed Description, with each claims standing on its own to represent separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. An aortic dissection system for treating a dissection within an aorta of a patient, the aortic dissection system comprising:
   an aortic dissection implant comprising:
      an expandable support structure having a proximal end and a distal end, the expandable support structure sized and configured to be positioned within an ascending portion of the aorta and sized and configured to extend to within a descending portion of the aorta and apply radial force to the descending portion of the aorta when expanded;
      at least one layer provided over the expandable support structure comprising an atraumatic outer surface configured to engage an inner wall of the aorta adjacent a false lumen associated with the dissection; and
      an expandable interface structure at the distal end of the expandable support structure having a cross-sectional dimension larger than a cross-section dimension of the expandable support structure when both are expanded, the expandable interface structure comprising a metallic frame having a trilobe shape comprising three lobes sized and configured to expand within a corresponding left coronary sinus, a right coronary sinus and a non-coronary sinus, respectively, wherein the trilobe shape is configured to extend from within the left and right coronary sinus distal of a left and right coronary ostia, respectively, and from within the non-coronary sinus, proximally to a sinotubular junction to apply radial force to the left, right and non-coronary sinuses and the sinotubular junction when the expandable interface structure is expanded; wherein the at least one layer extends over the expandable support structure and the expandable interface structure, and wherein the at least one layer comprises a porous section and a non-porous section; and
   a delivery system configured to be inserted percutaneously into the patient and advanced into the patient's aorta, the delivery system comprising an outer sheath configured to receive the aortic dissection implant therein in a compressed configuration.

2. The system of claim 1, wherein the non-porous section is configured to extend across at least a portion of the dissection.

3. The system of claim 1, wherein the porous section comprises a porous layer provided over the expandable support structure and the non-porous section comprises a non-porous layer provided over the porous layer.

4. The system of claim 1, wherein the porous section is configured to permit blood flow from within the expandable support structure, through the porous section, and into the carotid arteries and the subclavian arteries.

5. The system of claim 1, wherein the non-porous section comprises an opening to allow blood to flow from within the expandable support structure, through the opening, and into the carotid and the subclavian arteries.

6. The system of claim 1, wherein the expandable support structure is pre-formed with a curvature to conform to the aortic arch.

7. The system of claim 1, wherein the comprises a porous layer configured to substantially cover the expandable support structure from the descending aorta to the sinotubular junction and the non-porous section comprises a non-porous layer partially covering the porous layer and configured to engage a wall of the ascending aorta on opposite sides of a tear of the dissection.

8. The system of claim 1, wherein the expandable interface structure comprises a wire frame.

9. The system of claim 1, wherein the at least one layer is configured to extend within the left and right coronary sinuses without blocking blood flow into the left and right coronary arteries.

10. The system of claim 1, wherein the non-porous section comprises a non-porous layer configured to be positioned across at least a portion of the dissection.

11. The system of claim 1, wherein the at least one layer is configured to expand to engage the inner wall of the aorta separately from expansion of the expandable support structure, and the delivery system is configured to sequentially deploy the at least one layer before the expandable support structure.

12. The system of claim 1, wherein the two lobes that are configured to extend within the left and right coronary sinuses are at least partially uncovered such that the left and right coronary ostia remain uncovered by the aortic dissection implant when in use.

13. The system of claim 1, wherein each of the three lobes is sized and configured to conform to a curvature of the sinuses when the expandable interface structure is expanded.

14. The system of claim 1, wherein each of the three lobes comprises a single apex at a distal end of the expandable anchoring structure configured to be positioned adjacent an aortic valve annulus of the patient.

15. The system of claim 1, wherein the expandable support structure comprises a metallic frame that extends continuously from the proximal end to the distal end of the expandable support structure and that is continuous with the metallic frame of the expandable interface structure.

16. The system of claim 15, wherein the expandable support structure and the expandable interface structure comprise separate frames.

17. The system of claim 15, wherein the expandable support structure and the expandable interface structure are formed from a single continuous wire.

18. An aortic dissection implant for treating a dissection within an aorta of a patient, the aortic dissection implant comprising:
   an expandable anchoring structure configured to be positioned within the aortic root of a patient and apply radial force to one or more of the sinuses of the aortic root and/or the sinotubular junction when expanded, wherein the expandable anchoring structure has a trilobe configuration comprising three lobes; and
   an elongate tubular structure having a proximal end configured to be positioned in the descending aorta and a distal end configured to be positioned in the ascending aorta, the sinotubular junction, or the aortic root, wherein the expandable anchoring structure is connected to or forms the distal end of the elongate tubular structure, wherein the elongate tubular structure comprises:
      an expandable support frame having a first length configured to extend from the descending aorta to at least the ascending aorta and curve along with a curvature of the aortic arch when expanded within the aorta, wherein the expandable support frame has a tubular shape when expanded and the expandable anchoring structure has a cross-sectional dimension larger than a cross-section dimension of the expandable support frame when expanded;

a first porous layer positioned over the expandable support frame having a second length configured to extend from the descending aorta at least partially through the aortic arch, the first porous layer comprising an atraumatic outer surface and configured to allow blood to flow into the carotid and subclavian arteries;

wherein expansion of the expandable support frame when positioned within the aorta expands the first porous layer such that the atraumatic outer surface of the first porous layer presses against an interior surface of the aorta and applies a radial force at least to the descending aorta; and a second non-porous layer positioned over the expandable support frame having a third length that is less than the first length, wherein the second non-porous layer is configured to be positioned within the ascending aorta and distal to the carotid and subclavian arteries in use, wherein the second layer is configured to be positioned against a length of a tear of the dissection.

19. The aortic dissection implant of claim 18, wherein the second length of the first porous layer is approximately the same as the first length of the expandable support frame.

20. The aortic dissection implant of claim 18, wherein one or both of the first porous layer and the second non-porous layer comprises a fabric material.

21. The aortic dissection implant of claim 18, wherein the expandable support frame comprises a wire, a coiled ribbon, a laser cut structure, or a braid.

22. The aortic dissection implant of claim 18, wherein the atraumatic outer surface of the first porous layer is configured to engage an interior surface of the aorta within the aortic arch and to allow blood flow from the aortic arch, through the first porous layer, and to the carotid and/or subclavian arteries.

23. The aortic dissection implant of claim 18, wherein the expandable anchoring structure comprises openings for allowing blood flow to the left and right coronary ostia.

24. The aortic dissection implant of claim 18, wherein the second non-porous layer is configured to be positioned over the expandable support frame within the ascending aorta.

25. The aortic dissection implant of claim 18, wherein the second non-porous layer is configured to extend from within the aortic root to within the ascending aorta in use.

26. The aortic dissection implant of claim 18, wherein the three lobes are sized and configured to extend from a location distal of a left and a right coronary ostia proximally to a sinotubular junction to apply radial force to the sinuses and the sinotubular junction when the expandable anchoring structure is expanded.

27. The aortic dissection implant of claim 18, wherein each of the three lobes is sized and configured to conform to a curvature of the sinuses when the expandable anchoring structure is expanded.

28. The aortic dissection implant of claim 18, wherein the expandable anchoring structure and the elongate tubular structure comprise a continuous metallic frame extending from the proximal end of the elongate tubular structure to the trilobe configuration of the expandable anchoring structure.

* * * * *

UNITED STATES PATENT AND TRADEMARK OFFICE
CERTIFICATE OF CORRECTION

PATENT NO. : 10,888,414 B2  
APPLICATION NO. : 16/824029  
DATED : January 12, 2021  
INVENTOR(S) : Arshad Quadri et al.

Page 1 of 1

It is certified that error appears in the above-identified patent and that said Letters Patent is hereby corrected as shown below:

On the Title Page

On page 3, in Column 2, item (56), U.S. Patent Documents, Line 37, delete "Pears0n" and insert --Pearson--.

In the Specification

In Column 2, Line 15, delete "on layer" and insert --one layer--.

In Column 4, Line 59, delete "frame. the" and insert --frame. The--.

In Column 12, Line 39, delete "multi-fillar" and insert --multi-filler--.

In Column 22, Line 55, delete "FIG." and insert --FIGS.--.

In the Claims

In Column 25, Line 64, Claim 7, after "wherein the" insert --porous section--.

Signed and Sealed this  
Twenty-third Day of March, 2021

Drew Hirshfeld  
*Performing the Functions and Duties of the*  
*Under Secretary of Commerce for Intellectual Property and*  
*Director of the United States Patent and Trademark Office*